(12) United States Patent
Shimizu et al.

(10) Patent No.: US 8,916,071 B2
(45) Date of Patent: Dec. 23, 2014

(54) CHROMENE COMPOUND AND CURABLE COMPOSITION

(71) Applicant: Tokuyama Corporation, Shunan (JP)

(72) Inventors: Yasutomo Shimizu, Shunan (JP); Shinobu Izumi, Shunan (JP); Junji Takenaka, Shunan (JP); Junji Momoda, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 0 days.

(21) Appl. No.: 14/346,724

(22) PCT Filed: Sep. 21, 2012

(86) PCT No.: PCT/JP2012/074998
§ 371 (c)(1),
(2), (4) Date: Mar. 22, 2014

(87) PCT Pub. No.: WO2013/042800
PCT Pub. Date: Mar. 28, 2013

(65) Prior Publication Data
US 2014/0225050 A1 Aug. 14, 2014

(30) Foreign Application Priority Data

Sep. 22, 2011 (JP) ................. 2011-207988

(51) Int. Cl.
| | |
|---|---|
| *G02B 5/23* | (2006.01) |
| *C07C 323/21* | (2006.01) |
| *C09K 9/02* | (2006.01) |
| *C07D 311/78* | (2006.01) |
| *F21V 9/00* | (2006.01) |
| *G02B 5/02* | (2006.01) |
| *G02C 7/10* | (2006.01) |
| *G02F 1/361* | (2006.01) |
| *G03B 11/00* | (2006.01) |
| *G02F 1/03* | (2006.01) |
| *G02F 1/07* | (2006.01) |

(52) U.S. Cl.
CPC ............... *C09K 9/02* (2013.01); *C07C 323/21* (2013.01); *C07D 311/78* (2013.01)
USPC ............ 252/586; 252/582; 359/241; 544/79; 544/129; 544/141; 544/143; 544/150; 544/154; 546/15; 548/407; 549/330; 549/382; 549/406; 549/502; 564/114; 564/426; 568/325; 568/633

(58) Field of Classification Search
USPC ............ 252/582, 586; 359/241; 544/79, 129, 544/141, 143, 150, 154; 546/15; 548/407; 549/330, 382, 406, 502; 564/114, 426; 568/325, 633
See application file for complete search history.

(56) References Cited

U.S. PATENT DOCUMENTS

| | | |
|---|---|---|
| 2009/0309076 A1 | 12/2009 | He et al. |
| 2012/0121934 A1 | 5/2012 | Takahashi et al. |
| 2014/0054520 A1 | 2/2014 | Takenaka et al. |

FOREIGN PATENT DOCUMENTS

| | | |
|---|---|---|
| JP | 11-49827 A | 2/1999 |
| WO | WO 01/60881 A2 | 8/2001 |
| WO | WO 2005/028465 A1 | 3/2005 |
| WO | WO 2010/065393 A1 | 6/2010 |
| WO | WO 2011/016582 A1 | 2/2011 |
| WO | WO 2012/121414 A1 | 9/2012 |

OTHER PUBLICATIONS

International Search Report, mailed Nov. 6, 2012, issued in PCT/JP2012/074998.
Clive et al. "Formal Radical Cyclization onto Benzene Rings: A General Method and Its Use in the Synthesis of ent-Nocardione A", J. Org Chem, vol. 69, 2004, pp. 3282-3293.
Gourdoupis et al. "A Direct and Versatile Synthesis of 5-(2-Di-n-Propylamino-Ethyl)-7-Methoxyindole", Synthetic Communications, vol. 23, No. 16, 1993, pp. 2241-2249.
International Preliminary Report on Patentability and English translation of the Written Opinion of the International Searching Authority dated Apr. 3, 2014 for Application No. PCT/JP2012/074998.

*Primary Examiner* — Bijan Ahvazi
(74) *Attorney, Agent, or Firm* — Birch, Stewart, Kolasch & Birch, LLP

(57) ABSTRACT

A chromene compound which has a sulfur-containing substituent represented by the following formula (2) at the 6-position and/or 7-position carbon atom of an indeno(2,1-f)naphtho(1,2-b)pyran structure and is excellent in photochromic properties and stability at a high temperature. In the formula (2), ring X is an aromatic hydrocarbon ring or aromatic heterocyclic ring, $R^3$ and $R^4$ are each independently an alkyl group, haloalkyl group, cycloalkyl group, alkoxy group, amino group, heterocyclic group containing a ring member nitrogen atom and bonded to the ring X bonded thereto via the nitrogen atom, halogen atom, aryloxy group or aryl group, and "a" is an integer of 0 to 4.

(2)

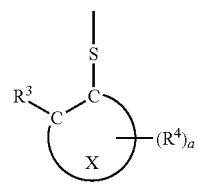

14 Claims, No Drawings

CHROMENE COMPOUND AND CURABLE COMPOSITION

TECHNICAL FIELD

The present invention relates to a novel chromene compound and use thereof.

BACKGROUND ART

Photochromism is the reversible function of a certain compound that it changes its color swiftly upon exposure to light including ultraviolet light such as sunlight or light from a mercury lamp and returns to its original color when it is put in the dark by stopping its exposure to light. A compound having this property is called "photochromic compound" and used as a material for photochromic plastic lenses.

For the photochromic compound used for this purpose, the following properties are required: (A) the degree of coloration at a visible light range before ultraviolet light is applied (to be referred to as "initial coloration" hereinafter) should be low, (B) the degree of coloration upon exposure to ultraviolet light (to be referred to as "color optical density" hereinafter) should be high, (C) the speed from the time when the application of ultraviolet light is started to the time when the color optical density reaches saturation (to be referred to as "color development sensitivity" hereinafter) should be high, (D) the speed from the stoppage of the application of ultraviolet light to the time when the compound returns to its original state (to be referred to as "fading speed" hereinafter) should be high, (E) the repeat durability of this reversible function should be high, (F) the solubility in a monomer composition which will become a host material after curing of the photochromic compound should be high so that its dispersibility in the host material in use becomes high, and (G) the compound should develop a color of a neutral tint such as brown or gray by itself.

As the photochromic compound which can satisfy these requirements, there are known chromene compounds having an indeno(2,1-f)naphtho(1,2-b)pyran structure represented by the following formula (I) as the basic skeleton (refer to a pamphlet of WO2005/028465, a pamphlet of WO2010/065393, a pamphlet of WO2011/016582 and the publication of US20090309706).

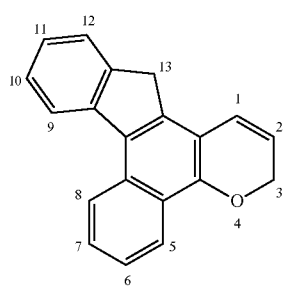

(I)

The inventors of the present invention demonstrated that out of these chromene compounds, chromene compounds having a sulfur-containing substituent represented by the following formula (II) are particularly excellent in initial coloration, color optical density, fading speed and developed hue (refer to a pamphlet of WO2011/016582).

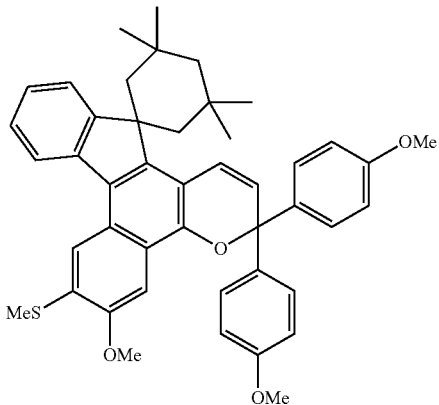

(II)

(In the formula, Me means a methyl group.)

The above pamphlet shows that a compound obtained by substituting a methylthio group at the 7-position of the chromene compound of the formula (II) by a phenylthio group has the same effect.

Although the above compounds are very excellent, when the inventors of the present invention conducted various studies, they found that when an optical article manufactured by using the above compound having a sulfur-containing substituent is kept at a high temperature, it yellows or its developed hue changes at the time of exposure according to the conditions. This suggests that restrictions may be imposed on a production process which requires a high-temperature treatment, or there may occur a problem with storage stability.

DISCLOSURE OF THE INVENTION

It is therefore an object of the present invention to provide a chromene compound which is excellent in photochromic properties and stability at a high temperature and has a sulfur-containing substituent. Stability at a high temperature may be simply referred to as "heat resistance".

The inventors of the present invention conducted intensive studies to attain the above object. As a result, they found that stability at a high temperature is greatly improved by introducing an arylthio group having a specific substituent into the 6-position and/or the 7-position of an indeno(2,1-f)naphtho (1,2-b)pyran structure and accomplished the present invention.

That is, the first invention is a chromene compound having a basic skeleton represented by the following formula (1).

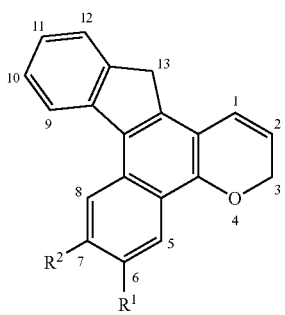

(1)

In the above formula, a combination of $R^1$ and $R^2$ is any one of (i), (ii) and (iii) below.
(i) Each of $R^1$ and $R^2$ is a sulfur-containing substituents represented by the following formula (2).

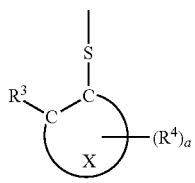

(In the above formula, ring X represented by the following formula is an aromatic hydrocarbon ring or aromatic heterocyclic ring, groups represented by $R^3$ and $R^4$ are each independently an alkyl group, haloalkyl group, cycloalkyl group, alkoxy group, amino group, heterocyclic group containing a ring member nitrogen atom and bonded to the ring X bonded thereto via the nitrogen atom, halogen atom, aryloxy group or aryl group, "a" is an integer of 0 to 4, and when "a" is 2 to 4, a plurality of $R^4$'s may be the same or different.)

(ii) $R^1$ is a sulfur-containing substituent represented by the above formula (2) and $R^2$ is a hydrogen atom, hydroxyl group, alkyl group, haloalkyl group, cycloalkyl group, alkoxy group, amino group, heterocyclic group containing a ring member nitrogen atom and bonded to the 7-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group.
(iii) $R^2$ is a sulfur-containing substituent represented by the above formula (2) and $R^1$ is a hydrogen atom, hydroxyl group, alkyl group, haloalkyl group, cycloalkyl group, alkoxy group, amino group, heterocyclic group containing a ring member nitrogen atom and bonded to the 6-position carbon atom via the nitrogen atom, cyano group, nitro group, formyl group, hydroxycarbonyl group, alkylcarbonyl group, alkoxycarbonyl group, halogen atom, aralkyl group, aralkoxy group or aryloxy group.

The second invention is a photochromic curable composition which comprises the chromene compound of the present invention and polymerizable monomers.

The third invention is a photochromic optical article having a polymer molded product comprising the chromene compound of the present invention dispersed therein as a constituent member.

The fourth invention is an optical article having an optical substrate all or part of at least one surface of which is covered with a polymer film comprising the chromene compound of the present invention dispersed therein as a constituent member.

The fifth invention is a naphthol compound represented by the formula (6) which will be given hereinafter.

BEST MODE FOR CARRYING OUT THE INVENTION

The chromene compound of the present invention has an indeno(2,1-f)naphtho(1,2-b)pyran structure represented by the following formula (1) as a basic skeleton.

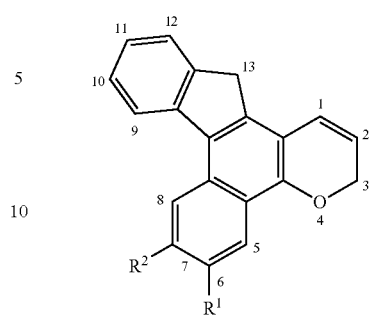

This compound has the biggest structural feature that it has a specific sulfur-containing substituent ($R^1$, $R^2$) at the 6-position and/or the 7-position carbon atom(s).

It is known that a chromene compound having an indeno (2,1-f)naphtho(1,2-b)pyran structure as the basic skeleton exhibits excellent photochromic properties. However, the heat resistance of a chromene compound into which a sulfur-containing substituent has been introduced has been unknown, and therefore it has been unknown that a chromene compound having a specific sulfur-containing substituent of the present invention has excellent photochromic properties and high heat resistance.

A detailed description is subsequently given of the compound of the present invention.

<Sulfur-Containing Substituent Substituting the 6-Position ($R^1$) and/or the 7-Position ($R^2$)>

The feature of the chromene compound of the present invention is that it has a specific sulfur-containing substituent, thereby producing an excellent effect.

This sulfur-containing substituent is represented by the following formula (2).

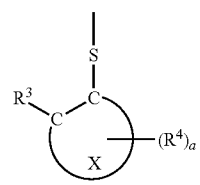

In the above formula (2), the ring X represented by the following formula is an aromatic hydrocarbon ring or aromatic heterocyclic ring.

The above aromatic hydrocarbon ring is preferably an aromatic hydrocarbon ring having 6 to 18 carbon atoms. Preferred examples thereof include benzene ring, naphthalene ring, fluorene ring and phenanthrene ring. Out of these, benzene ring and naphthalene ring are particularly preferred because initial coloration is little.

The above aromatic heterocyclic ring is preferably a five-membered ring or six-membered ring containing oxygen, sulfur or nitrogen, or heterocyclic ring having a benzene ring condensed to these. Preferred examples thereof include nitrogen-containing heterocyclic rings such as pyridine, quinolone, pyrroline and indoline, oxygen-containing heterocyclic rings such as furan and benzofuran, and sulfur-containing heterocyclic rings such as thiophene and benzothiophene.

In the above formula (2), groups represented by $R^3$ and $R^4$ are each independently an alkyl group, haloalkyl group, cycloalkyl group, alkoxy group, amino group, heterocyclic group containing a ring member nitrogen atom and bonded to the ring X, that is, an aromatic hydrocarbon ring or aromatic heterocyclic ring bonded thereto via the nitrogen atom, halogen atom, aryloxy group or aryl group.

The above alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The above haloalkyl group is preferably an alkyl group having 1 to 6 carbon atoms and substituted by a fluorine atom, chlorine atom or bromine atom. Preferred examples of the haloalkyl group include trifluoromethyl group, tetrafluoroethyl group, chloromethyl group, 2-chloroethyl group and bromomethyl group.

The above cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The above alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

The above amino group is not limited to a primary amino group (—$NH_2$) and may be a secondary or tertiary amino group obtained by substituting one or two hydrogen atoms of a primary amino group. Examples of the substituent of the amino group include alkyl groups having 1 to 6 carbon atoms, haloalkyl groups having 1 to 6 carbon atoms, alkoxy groups having 1 to 6 carbon atoms, cycloalkyl groups having 3 to 7 carbon atoms, aryl groups having 6 to 14 carbon atoms and heteroaryl groups having 4 to 14 carbon atoms. Preferred examples of the amino group include amino group, methylamino group, dimethylamino group, ethylamino group, diethylamino group, phenylamino group and diphenylamino group.

Examples of the above heterocyclic group containing a ring member nitrogen atom and bonded to the ring X, that is, an aromatic hydrocarbon ring or aromatic heterocyclic ring bonded thereto via the nitrogen atom include aliphatic heterocyclic groups such as morpholino group, piperidino group, pyrrolidinyl group, piperazino group and N-methylpiperazino group, and aromatic heterocyclic groups such as indolinyl group. Further, the heterocyclic group may have a substituent. A preferred example of the substituent is an alkyl group. Preferred examples of the heterocyclic group having a substituent include 2,6-dimethylmorpholino group, 2,6-dimethylpiperidino group and 2,2,6,6-tetramethylpiperidino group.

Examples of the above halogen atom include fluorine atom, chlorine atom, bromine atom and iodine atom.

The above aryloxy group is preferably an aryloxy group having 6 to 12 carbon atoms. Preferred examples of the aryloxy group include phenyloxy group and naphthyloxy group.

The above aryl group is preferably an aryl group having 6 to 14 carbon atoms. Preferred examples of the aryl group include phenyl group, 1-naphthyl group and 2-naphthyl group.

1 to 7 hydrogen atoms, particularly preferably 1 to 4 hydrogen atoms of the benzene ring or naphthalene ring of each of the aryloxy group and the aryl group may be substituted by the above alkyl group, haloalkyl group, cycloalkyl group, alkoxy group, amino group or halogen atom.

In the above formula (2), "a" is an integer of 0 to 4 indicative of the number of $R^4$'s. When "a" is 2 to 4, a plurality of $R^4$'s may be the same or different.

The biggest feature of the chromene compound of the present invention is that it has a sulfur-containing substituent represented by the above formula (2), thereby obtaining excellent heat resistance. It was found through studies of this time that a chromene compound having a sulfur-containing substituent (different from $R^3$) different from the chromene compound of the present invention tends to yellows at a high temperature and its developed hue tends to change at the time of exposure. The inventors of the present invention assume that the cause of this is that a sulfur atom contained in the sulfur-containing substituent is oxidized by oxygen contained in air. Meanwhile, in the present invention, firstly, it is assumed that the sulfur-containing substituent represented by the above formula (2) becomes a steric barrier to the sulfur atom in the formula (2) and oxygen hardly contacts the sulfur atom. Secondly, it is assumed that as $R^3$ is existent, the electron density of the sulfur atom lowers, thereby suppressing oxidation. It is considered that there are two causes of reducing the electron density. As the first one, it is assumed that the ring X in the above formula (2) and the aromatic ring bonded to the sulfur-containing substituent represented by the above formula (2) are hardly arranged on the same plane due to the existence of $R^3$ with the result that the resonance effect deteriorates, resulting in the reduction of the electron density of the sulfur atom. As the second one, it is assumed that the bonding distance between the sulfur atom and the ring X becomes long due to the existence of $R^3$ with the result that the resonance effect deteriorates, resulting in the reduction of the electron density of the sulfur atom. The reduction of the electron density is confirmed from the electron density of a sulfur atom in two model compounds shown in Table 1 below (electron density obtained by molecular orbital calculation).

TABLE 1

| Model compound | 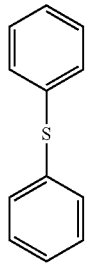 | 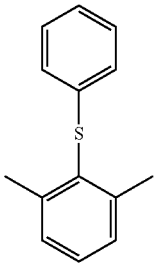 |
|---|---|---|
| Electron density | −0.285 | −0.185 |

A density functional theory was used and B3LYP/6-31G (d, p) was used as a functional for the molecular orbital calculation of the above model compounds.

As shown in Table 1, the non-substituted model compound has a sulfur atom electron density of −0.285 (V) whereas the model compound having a methyl group introduced at the ortho-position has a sulfur atom electron density of −0.185 (V). It is understood from this result that the sulfur-containing substituent having a substituent at the ortho-position (sulfur-containing substituent represented by the above formula (2)) is hardly oxidized due to the reduction of the sulfur atom electron density.

Therefore, it is preferred that the substituent represented by $R^3$ should be a group which is sterically more bulky than a hydrogen atom, and the above-described substituents are preferably used. $R^3$ is preferably selected from alkyl groups, alkoxy groups and aryl groups from the viewpoints of a high level of durability and the easy acquisition of raw materials. Out of these, methyl group, ethyl group, n-propyl group, isopropyl group, n-butyl group, sec-butyl group, tert-butyl group, methoxy group, ethoxy group, n-propoxy group, isopropoxy group, n-butoxy group and phenyl group are particularly preferred.

In the above formula (2), the substituent represented by $R^4$ functions as a steric barrier like $R^3$ when it substitutes on a carbon atom adjacent to the carbon atoms bonded to the sulfur atom. Therefore, the same substituent as $R^3$ is preferably used as $R^4$.

Also, it is possible to control the developed hue at the time of exposure of the chromene compound of the present invention by $R^4$ substituting the other position. For this purpose, an alkyl group, alkoxy group, amino group or heterocyclic group containing a ring member nitrogen atom and bonded to the ring X, that is, an aromatic hydrocarbon ring or aromatic heterocyclic ring bonded thereto via the nitrogen atom, all of which have high electron donating ability, are preferably used. Out of these substituents, methyl group, ethyl group, methoxy group, ethoxy group, n-propoxy group, isopropoxy group, n-butoxy group, dimethylamino group, diethylamino group, morpholino group, piperidino group and pyrrolidinyl group are particularly preferred from the viewpoint of the easy acquisition of raw materials and synthesis ease.

The ring X in the above formula (2) is particularly preferably an aromatic hydrocarbon ring from the viewpoint of the easy acquisition of raw materials and most preferably a benzene ring or naphthalene ring from the viewpoint of little initial coloration.

Preferred examples of the sulfur-containing substituent represented by the above formula (2) are given below.

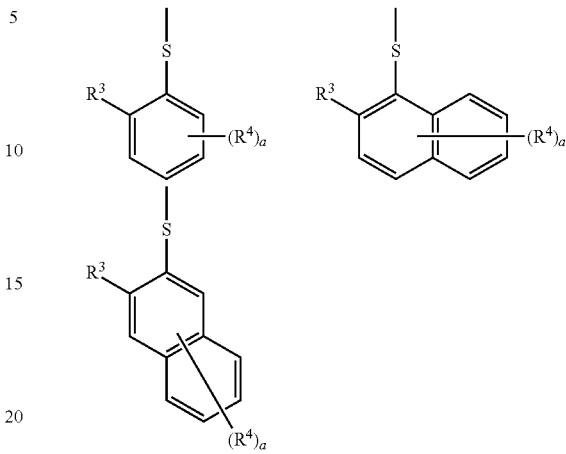

In the above formulas, "a" is an integer of 0 to 4, preferably 0 to 2.

More preferred examples are given below.

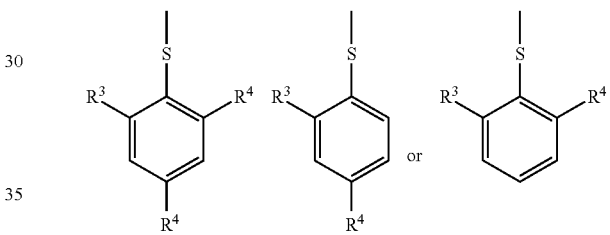

Further, preferred examples of the sulfur-containing substituent represented by the above formula (2) are shown in Table 2 below. The electron density of the sulfur atom measured by the same method as above is also shown in the table. Me means a methyl group.

TABLE 2

| R = | | | | |
|---|---|---|---|---|
| Electron density | −0.238 | −0.185 | −0.193 | −0.171 |

TABLE 2-continued

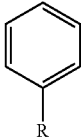

| R = | 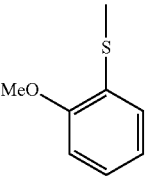 | 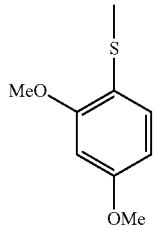 | 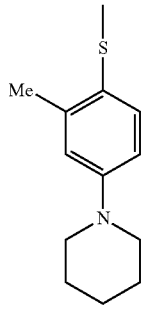 | 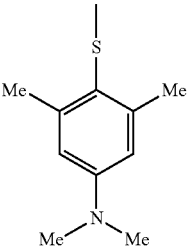 |
|---|---|---|---|---|
| Electron density | −0.206 | −0.207 | −0.239 | −0.217 |

| R = | 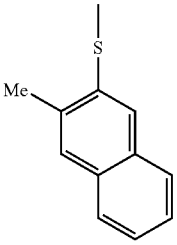 | 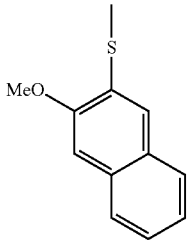 | 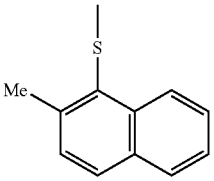 | 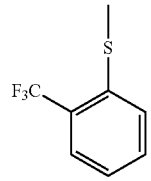 |
|---|---|---|---|---|
| Electron density | −0.221 | −0.203 | −0.194 | −0.229 |

In the above formula (1), a combination of the 6-position substituent $R^1$ and the 7-position substituent $R^2$ is anyone of the following combinations (i), (ii) and (iii).

(i) Both of $R^1$ and $R^2$ are sulfur-containing substituents represented by the above formula (2).

(ii) R is the above sulfur-containing substituent and $R^2$ is a hydrogen atom, hydroxyl group, alkyl group, haloalkyl group, cycloalkyl group, alkoxy group, amino group, heterocyclic group containing a ring member nitrogen atom and bonded to the 7-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group.

(iii) $R^2$ is the above sulfur-containing substituent, and $R^1$ is a hydrogen atom, hydroxyl group, alkyl group, haloalkyl group, cycloalkyl group, alkoxy group, amino group, heterocyclic group containing a ring member nitrogen atom and bonded to the 6-position carbon atom via the nitrogen atom, cyano group, nitro group, formyl group, hydroxycarbonyl group, alkylcarbonyl group, alkoxycarbonyl group, halogen atom, aralkyl group, aralkoxy group or aryloxy group or aryl group.

The alkyl group, the haloalkyl group, the cycloalkyl group, the alkoxy group, the amino group, the heterocyclic group containing a ring member nitrogen atom and bonded to the 7-position or 6-position carbon atom via the nitrogen atom, the aryloxy group and the aryl group in the combinations (ii) and (iii) are the same as those explained for $R^3$ and $R^4$ in the above formula (2). As a matter of course, the heterocyclic group containing a ring member nitrogen atom and bonded to the 7-position or 6-position carbon atom via the nitrogen atom is the same as the heterocyclic group containing a ring member nitrogen atom and bonded to the ring X, that is, an aromatic hydrocarbon ring or aromatic heterocyclic ring bonded thereto via the nitrogen atom as explained for $R^3$ and $R^4$.

The above alkylcarbonyl group is preferably an alkylcarbonyl group having 2 to 7 carbon atoms. Preferred examples of the alkylcarbonyl group include acetyl group and ethylcarbonyl group.

The above alkoxycarbonyl group is preferably an alkoxycarbonyl group having 2 to 7 carbon atoms. Preferred examples of the alkoxycarbonyl group include methoxycarbonyl group and ethoxycarbonyl group.

The above aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The above aralkoxy group is preferably an aralkoxy group having 7 to 11 carbon atoms. Preferred examples of the aralkoxy group include benzyloxy group and naphthylmethoxy group.

1 to 5 hydrogen atoms of the benzene ring or 1 to 7 hydrogen atoms, particularly preferably 1 to 4 hydrogen atoms of the naphthalene ring of each of the aralkyl group and the aralkoxy group may be substituted by the above hydroxyl group, alkyl group, haloalkyl group, cycloalkyl group, alkoxy group, amino group, cyano group, nitro group or halogen atom.

<Preferred Chromene Compound>

Out of the chromene compounds of the present invention, a chromene compound represented by the following formula (3) is preferred as it develops a color of a neutral tint and has high color optical density, high fading speed and excellent durability of photochromic properties.

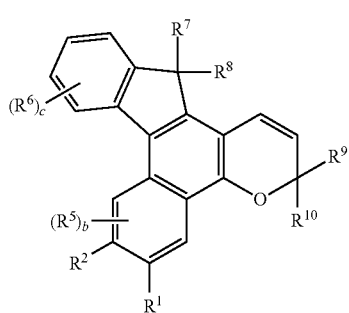

(3)

The substituents of the chromene compound represented by the above formula (3) will be explained hereinbelow.

<Substituents $R^1$ and $R^2$>

$R^1$ and $R^2$ are as defined in the formula (1). When a combination of $R^1$ and $R^2$ is (i), $R^1$ and $R^2$ may be the same or different.

<Substituents $R^5$ and $R^6$>

$R^5$ and $R^6$ are each independently a hydroxyl group, alkyl group, haloalkyl group, cycloalkyl group, alkoxy group, amino group, heterocyclic group containing a ring member nitrogen atom and bonded to an aromatic ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group or sulfur-containing substituent represented by the above formula (2).

Out of these substituents, the alkyl group, the haloalkyl group, the cycloalkyl group, the alkoxy group and the amino group are preferably the same as those enumerated for the above $R^3$ and $R^4$.

The alkylcarbonyl group, the alkoxycarbonyl group, the halogen atom, the aralkyl group, the aralkoxy group, the aryloxy group, the aryl group and the sulfur-containing substituent represented by the above formula (2) are preferably the same as those enumerated for the above $R^1$ and $R^2$.

Preferred examples of the above heterocyclic group containing a ring member nitrogen atom and bonded to an aromatic ring bonded thereto via the nitrogen atom include aliphatic heterocyclic groups such as morpholino group, piperidino group, pyrrolidinyl group, piperazino group and N-methylpiperazino group, and aromatic heterocyclic groups such as indolinyl group. Further, the heterocyclic group may have a substituent. A preferred example of the substituent is an alkyl group. Preferred examples of the heterocyclic group having a substituent include 2,6-dimethylmorpholino group, 2,6-dimethylpiperidino group and 2,2,6,6-tetramethylpiperidino group.

"b" is an integer of 0 to 2 indicative of the number of $R^5$'s. When "b" is 2, two $R^5$'s may be the same or different. "c" is an integer of 0 to 4 indicative of the number of $R^6$'s. When "c" is an integer of 2 to 4, a plurality of $R^6$'s may be the same or different.

$R^5$ preferably has a sterically small substituent as a high fading speed is obtained. Therefore, it is particularly preferred that "b" should be 0 and there should be no substituent $R^5$.

As for $R^6$, it is preferred that "c" should be 0, that is, there should be no substituent $R^6$, or $R^6$ should be a haloalkyl group or cyano group since a high fading speed is obtained. Stated more specifically, it is particularly preferable that there should be no $R^6$, or $R^6$ should be a trifluoromethyl group or cyano group. In order to obtain high color optical density, $R^6$ is preferably an alkyl group or alkoxy group. In either case, to obtain a great effect, the substituent $R^6$ is preferably bonded to the 11-position carbon atom.

Even when there are a plurality of $R^5$'s and a plurality of $R^6$'s, preferred $R^5$ and $R^6$ are the same as those explained above.

($R^7$ and $R^8$)

$R^7$ and $R^8$ are each independently a hydrogen atom, hydroxyl group, alkyl group, haloalkyl group, cycloalkyl group, alkoxy group, alkoxyalkyl group, formyl group, hydroxycarbonyl group, alkylcarbonyl group, alkoxycarbonyl group, halogen atom, aralkyl group, aralkoxy group, aryloxy group or aryl group.

The alkyl group, the haloalkyl group, the cycloalkyl group, the alkoxy group, the alkycarbonyl group, the alkoxycarbonyl group, the halogen atom, the aralkyl group, the aralkoxy group, the aryloxy group and the aryl group are the same as those explained for the above $R^1$, $R^2$, $R^3$ and $R^4$.

Preferred examples of the above alkoxyalkyl group include methoxymethyl group, methoxyethyl group, methoxy-n-propyl group, methoxy-n-butyl group, ethoxyethyl group and n-propoxypropyl group.

$R^7$ and $R^8$, together with the 13-position carbon atom bonded thereto may form an aliphatic hydrocarbon ring having 3 to 20 ring member carbon atoms, condensed polycyclic ring having an aliphatic hydrocarbon ring, aromatic hydrocarbon ring or aromatic heterocyclic ring condensed to the above aliphatic hydrocarbon ring, heterocyclic ring having 3 to 20 ring member atoms, or condensed polycyclic ring having an aromatic hydrocarbon ring or aromatic heterocyclic ring condensed to the above heterocyclic ring.

Examples of the above aliphatic hydrocarbon ring include cyclopentane ring, cyclohexane ring, cyclooctane ring, cycloheptane ring, norbornane ring, bicyclononane ring and adamantane ring.

Examples of the above condensed polycyclic ring having an aliphatic hydrocarbon ring, aromatic hydrocarbon ring or aromatic heterocyclic ring condensed to the above aliphatic hydrocarbon ring include fluorene ring and phenanthrene ring.

Examples of the above heterocyclic ring include thiophene ring, furan ring and pyridine ring.

Examples of the above condensed polycyclic ring having an aromatic hydrocarbon ring or aromatic heterocyclic ring condensed to the above heterocyclic ring include phenylfuran ring and biphenylthiophene ring.

(Particularly Preferred $R^7$ and $R^8$>

In the present invention, $R^7$ and $R^8$ are preferably hydroxyl groups, alkyl groups, alkoxy groups or groups which form a ring together with the 13-position carbon atom bonded thereto. A preferred example of the alkyl group is a methyl group, and a preferred example of the alkoxy group is a methoxy group. To reduce initial coloration by thermochromism and increase the fading speed while retaining high double peak characteristic, out of the above preferred substituents, $R^7$ and $R^8$ are preferably groups which form a ring together with the 13-position carbon atom bonded thereto. They are more preferably the above aliphatic hydrocarbon ring or the condensed polycyclic ring having an aromatic hydrocarbon ring or aromatic heterocyclic ring condensed to the above aliphatic hydrocarbon ring because the fading speed in particular becomes high. They are particularly preferably groups which form the above aliphatic hydrocarbon ring because initial coloration by thermochromism is reduced.

The aliphatic hydrocarbon ring formed by $R^7$ and $R^8$ is particularly preferably a nonsubstituted aliphatic hydrocarbon ring or an aliphatic hydrocarbon ring having at least one substituent selected from the group consisting of alkyl group, haloalkyl group, cycloalkyl group, alkoxy group, amino group, aralkyl group, aryl group and halogen atom. The alkyl group, the haloalkyl group, the cycloalkyl group, the alkoxy group, the amino group, the aralkyl group, the aryl group and the halogen atom are the same as those explained for $R^3$ and $R^4$.

More preferred examples of $R^7$ and $R^8$ include monocyclic rings such as cyclohexane ring, cyclooctane ring and cycloheptane ring, bicyclo rings such as norbornane ring, bicyclo[3,2,1]octane ring, bicyclo[4,2,0]octane ring, bicyclo[3,3,0]octane ring, bicyclo[3,3,1]nonane ring, bicyclo[4,3,0]nonane ring and bicyclo[6,3,0]undecane ring, tricyclo rings such as adamantane ring, and rings obtained by substituting these rings by at least one lower alkyl group having 4 or less carbon atoms such as methyl group. Out of these, monocyclic rings or bicyclo rings are particularly preferred because initial coloration by thermochromism is reduced while high double peak characteristic and high fading speed are retained.

In the present invention, most preferred typical examples of the monocyclic ring and bicyclo ring formed by bonding $R^7$ and $R^8$ include rings represented by the following formulas. In the following formulas, the carbon atom denoted by 13 is the 13-position carbon atom. Me and Et mean methyl group and ethyl group, respectively.

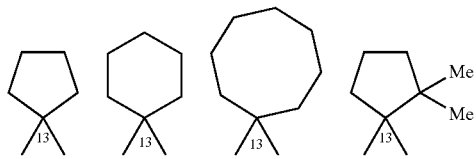

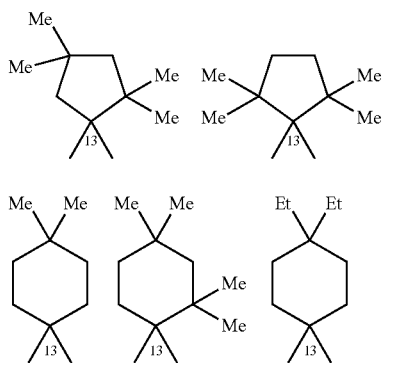

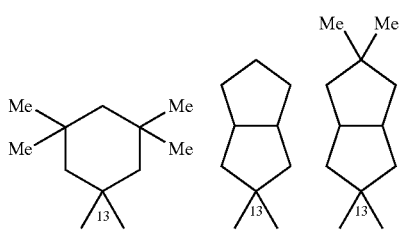

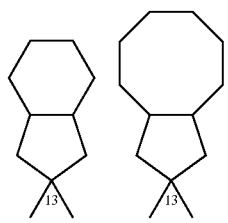

<$R^9$ and $R^{10}$>

$R^9$ and $R^{10}$ are each independently a group represented by the following formula (4), group represented by the following formula (5), aryl group, heteroaryl group or alkyl group.

$R^{11}$ in the above formula (4) is an aryl group or heteroaryl group. Examples of the aryl group are the same as those explained for $R^3$ and $R^4$. The heteroaryl group is preferably a heteroaryl group having 4 to 12 carbon atoms. Preferred examples of the heteroaryl group include thienyl group, furyl group, pyrrolyl group, pyridyl group, benzothienyl group, benzofuryl group and benzopyrrolyl group.

$R^{12}$ is a hydrogen atom, alkyl group or halogen atom. Preferred examples of the alkyl group include methyl group, ethyl group and propyl group. Examples of the halogen atom include fluorine atom, chlorine atom, bromine atom and iodine atom.

"m" is an integer of 1 to 3. "m" is preferably 1 from the viewpoint of the acquisition of raw materials.

Preferred examples of the group represented by the above formula (4) include phenyl-ethenyl group, (4-(N,N-dimethylamino)phenyl)-ethenyl group, (4-morpholinophenyl)-ethenyl group, (4-piperidinophenyl)-ethenyl group, (4-methoxyphenyl)-ethenyl group, (2-methoxyphenyl)-ethenyl group, phenyl-1-methylethenyl group, (4-methoxyphenyl)-1-methylethenyl group, phenyl-1-fluoroethenyl group, (4-(N,N,-dimethylamino)phenyl)-1-fluoroethenyl group, 2-thienyl-ethenyl group, 2-furyl-ethenyl group, 2-(N-methyl)pyrrolinyl-ethenyl group, 2-benzothienyl-ethenyl group, 2-benzofuranyl-ethenyl group and 2-(N-methyl)indolyl-ethenyl group.

In the above formula (5), $R^{13}$ is an aryl group or heteroaryl group. These groups are considered as the same as those for $R^{11}$. "n" is an integer of 1 to 3. From the viewpoint of the easy acquisition of raw materials, "n" is preferably 1.

Preferred examples of the group represented by the above formula (5) include phenyl-ethynyl group, (4-(N,N-dimethylamino) phenyl)-ethynyl group, (4-morpholinophenyl)-ethynyl group, (4-piperidinophenyl)-ethynyl group, (4-methoxyphenyl)-ethynyl group, (4-methylphenyl)-ethynyl group, (2-methoxyphenyl)-ethynyl group, 2-thienyl-ethynyl group, 2-furyl-ethynyl group, 2-(N-methyl)pyrrolinyl-ethynyl group, 2-benzothienyl-ethynyl group, 2-benzofuranyl-ethynyl group and 2-(N-methyl)indolyl-ethynyl group, Examples of the aryl group, the heteroaryl group and the alkyl group represented by $R^9$ and $R^{10}$ are the same as those explained for $R^3$ and $R^4$, and $R^{11}$ and $R^{12}$.

$R^9$ and $R^{10}$ may form an aliphatic hydrocarbon ring together with the carbon atom bonded thereto.

Preferred examples of the aliphatic hydrocarbon ring include adamantane ring, bicyclononane ring, norbornane ring and fluorene ring.

In order for the chromene compound of the above formula (2) to exhibit excellent photochromic properties (double peak characteristic and fading speed), desirably, at least one, preferably both of $R^9$ and $R^{10}$ are aryl groups or heteroaryl groups. Particularly preferably, at least one, preferably both of $R^9$ and $R^{10}$ are each any one of the following groups (iv) to (vii):

(iv) an aryl group or heteroaryl group having an alkyl group or alkoxy group as a substituent;

(v) an aryl group or heteroaryl group having an amino group as a substituent;

(vi) an aryl group or heteroaryl group having a heterocyclic group which has a nitrogen atom as a ring member hetero atom and is bonded to an aryl group or heteroaryl group via the nitrogen atom as a substituent; and (vii) an aryl group or heteroaryl group having a condensed heterocyclic group obtained by condensing an aromatic hydrocarbon ring or aromatic heterocyclic ring to the heterocyclic group in (vi) as a substituent.

The position of the substituent substituting the aryl group in (iv) to (vii) and the total number of substituents are not particularly limited. In order to obtain excellent photochromic properties, when the aryl group is a phenyl group, the substitution position is preferably the 3-position or 4-position, and the number of substituents is preferably 1. Preferred examples of this aryl group include 4-methylphenyl group, 4-methoxyphenyl group, 3,4-dimethoxyphenyl group, 4-n-propoxyphenyl group, 4-(N,N-dimethylamino)phenyl group, 4-(N,N-diethylamino)phenyl group, 4-(N,N-diphenylamino) phenyl group, 4-morpholinophenyl group, 4-piperidinophenyl group, 3-(N,N-dimethylamino)phenyl group and 4-(2,6-dimethylpiperidino)phenyl group.

The position of the substituent substituting the heteroaryl group in (iv) to (vii) and the total number of substituents are not particularly limited. The number of the substituents is preferably 1. Preferred examples of the heteroaryl group include 4-methoxythienyl group, 4-(N,N-dimethylamino) thienyl group, 4-methylfuryl group, 4-(N,N-diethylamino) furyl group, 4-(N,N-diphenylamino) thienyl group, 4-morpholinopyrrolinyl group, 6-piperidinobenzothienyl group and 6-(N,N-dimethylamino)benzofuranyl group.

<Particularly Preferred Chromene Compound>

Particularly preferred examples of the chromene compound in the present invention include the following compounds.

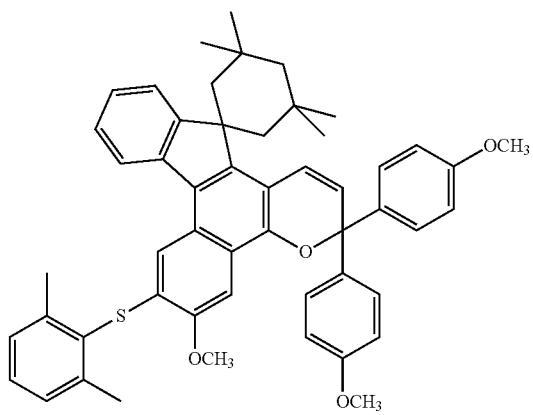

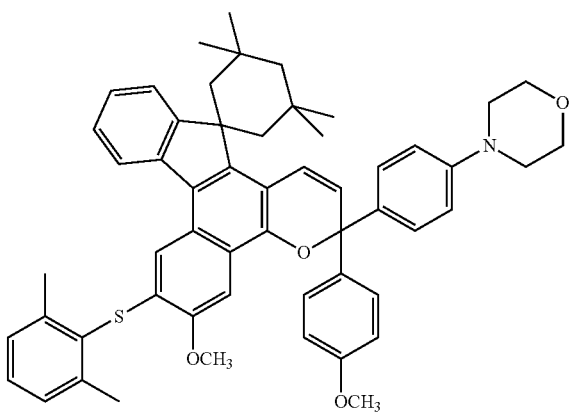

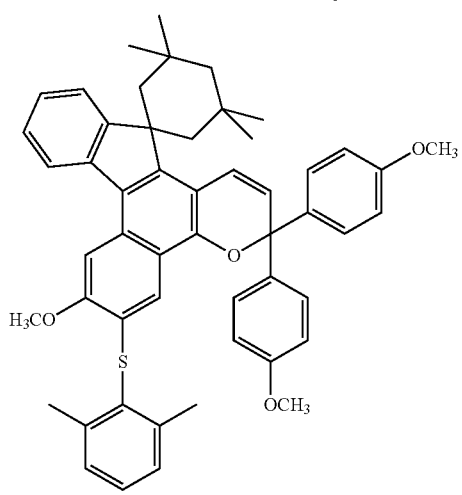

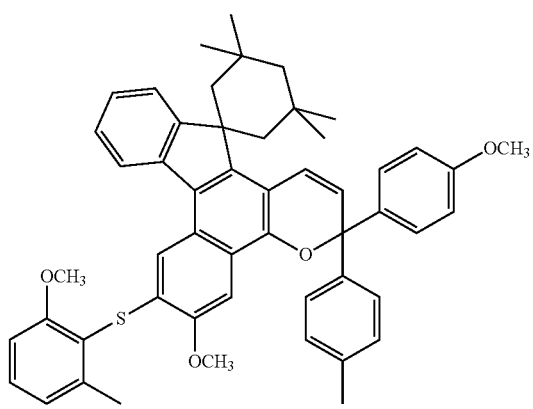

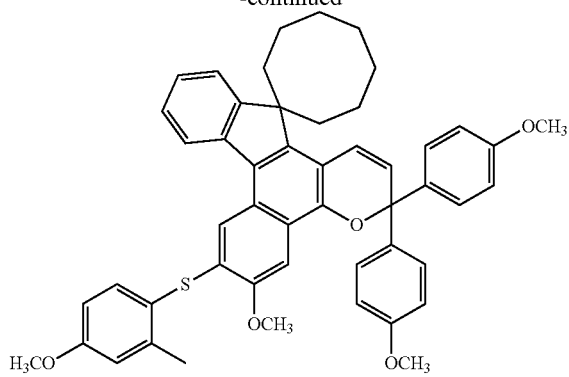

(Identification of Chromene Compound)

The chromene compound of the present invention is generally existent as an achromatic, light yellow or light green solid or viscous liquid at normal temperature and normal pressure and can be confirmed by the following means (1) to (3).

(1) When the proton nuclear magnetic resonance spectrum ($^1$H-NMR) of the chromene compound is measured, peaks based on an aromatic proton and an alkene proton appear at δ of around 5.5 to 9.0 ppm and peaks based on the protons of an alkyl group and an alkylene group appear at δ of around 0.5 to 4.5 ppm. By comparing these spectral intensities relatively, the number of the protons of bonds can be known.

(2) The composition of a corresponding product can be determined by elemental analysis.

(3) When the $^{13}$C-nuclear magnetic resonance spectrum ($^{13}$C-NMR) of the chromene compound is measured, a peak based on the carbon of an aromatic hydrocarbon group appears at δ of around 110 to 160 ppm, peaks based on the carbons of an alkene and an alkyne appear at δ of around 80 to 140 ppm, and peaks based on the carbons of an alkyl group and an alkylene group appear at δ of around 20 to 80 ppm.

<Production of Chromene Compound>

The process for producing the chromene compound of the present invention is not particularly limited and may be any synthesis process. For example, the chromene compound represented by the above formula (1) can be advantageously produced by the following process.

That is, the chromene compound of the present invention can be advantageously produced by reacting a naphthol compound represented by the following formula (6) with a propargyl alcohol compound represented by the following formula (7) in the presence of an acid catalyst.

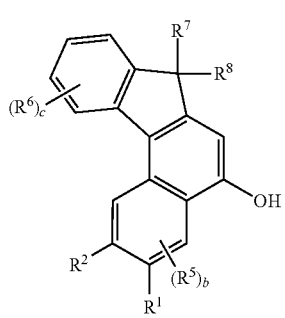

In the above formula, $R^1$, $R^2$, $R^5$, $R^6$, $R^7$, $R^8$, "b" and "c" are as defined in the above formula (3).

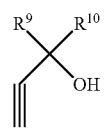

In the above formula, $R^9$ and $R^{10}$ are as defined in the above formula (3).

The reaction ratio of the naphthol compound to the propargyl alcohol compound is selected from a wide range, preferably from 1:10 to 10:1 (molar ratio). As the acid catalyst is used sulfuric acid, benzenesulfonic acid, p-toluenesulfonic acid or acid alumina. The acid catalyst is preferably used in an amount of 0.1 to 10 parts by weight based on 100 parts by weight of the total of the naphthol compound and the propargyl alcohol compound. The reaction temperature is preferably 0 to 200° C. An aprotic organic solvent such as N-methylpyrrolidone, dimethyl formamide, tetrahydrofuran, benzene or toluene is preferably used as the solvent. The method of purifying the product obtained through the above reaction is not particularly limited. For example, the obtained product can be purified by carrying out silica gel column purification and further recrystallization.

The naphthol compound represented by the above formula (6) is provided as a novel compound by the present invention. In the formula (6), $R^1$, $R^2$, $R^5$, $R^6$, $R^7$, $R^8$, "b" and "c" are as defined in the above formula (3). Therefore, it should be understood that the above explanation of the formula (3) is directly applied to these groups and parts.

In the present invention, preferred examples of the naphthol compound represented by the formula (6) include the following compounds.

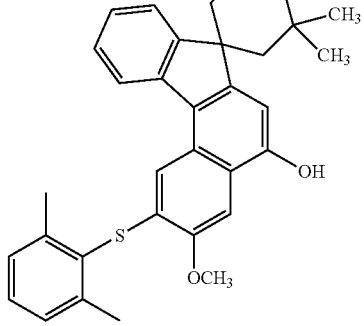

-continued

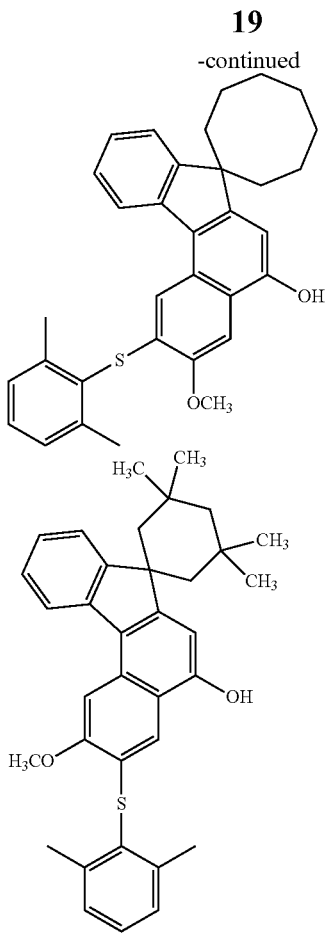

The naphthol compound can be synthesized in accordance with reaction methods described in research papers such as Journal of Organic Chemistry 69(10)3282-3293; 2004, Synthetic Communications 23(16)2241-2249 (1993) and WO01/60881.

(Process for Synthesizing Naphthol Compound)

Although the process for synthesizing the naphthol compound represented by the above formula (6) is not particularly limited, it can be synthesized as follows, for example.

To begin with, benzene compounds represented by the following formulas (8a) and (8b) can be purchased as commercial products ($R^1$, $R^2$, $R^5$ and "b" are as defined in the above formula (3).)

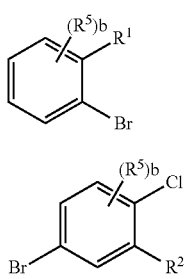

(8a)

(8b)

The compound (8a) and the acid chloride of the following formula (9) are reacted with each other to obtain a compound represented by the following formula (10a).

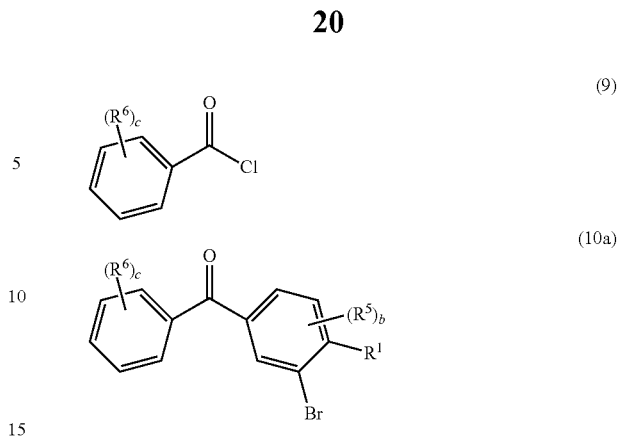

A Grignard reagent is prepared from the compound (8b) and reacted with the acid chloride of the above formula (9) to obtain a compound represented by the following formula (10b).

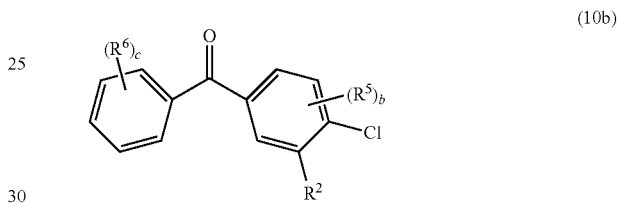

The bromine atom of the formula (10a) and the chlorine atom of the formula (10b) are converted into desired $R^2$ and $R^1$ by using a Buchwald-Hartwig cross-coupling reaction to obtain a compound represented by the following formula (11).

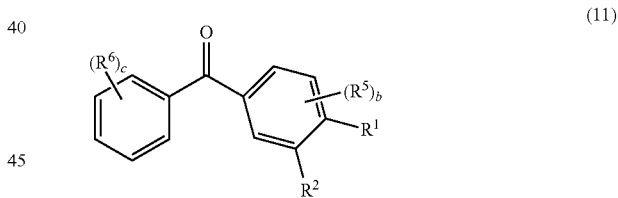

The above compound (II) is subjected to a Stobbe reaction and a cyclization reaction to obtain a compound represented by the following formula (12).

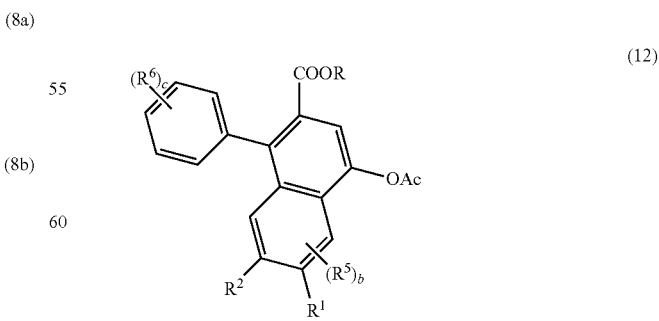

In the compound of the formula (12), R is a group derived from a diester compound used in the Stobbe reaction. Then, the compound (12) is hydrolyzed by using an alkali or acid to obtain a carboxylic acid represented by the following formula (13).

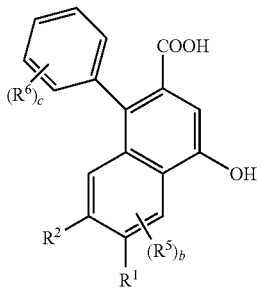
(13)

This carboxylic acid is benzylated by using a base such as potassium carbonate and benzyl chloride and then hydrolyzed by using an alkali or acid to obtain a benzyl-protected carboxylic acid represented by the following formula (14).

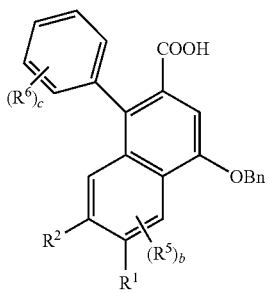
(14)

In the above formula, Bn means a benzyl group. This benzyl-protected carboxylic acid is converted into an amine by a method such as Curtius rearrangement, Hofmann rearrangement or Lossen rearrangement, and a diazonium salt is prepared from the amine. This diazonium salt is converted into a bromide through a Sandmeyer reaction or the like, and the obtained bromide is reacted with magnesium or lithium to prepare an organic metal reagent. This organic metal reagent is reacted with a ketone represented by the following formula (15) at −10 to 70° C. in an organic solvent for 10 minutes to 4 hours to obtain a compound represented by the following formula (16).

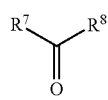
(15)

In the above formula, $R^7$ and $R^8$ are as defined in the above formula (3).

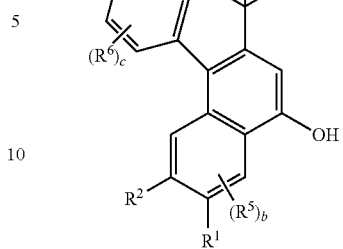
(16)

The compound (16) is reacted at 10 to 120° C. for 10 minutes to 2 hours under a neutral to acid condition to spironize an alcohol, thereby making it possible to synthesize the naphthol compound of the above formula (6) of interest. In the above reaction, the reaction ratio of the above organic metal reagent to the ketone represented by the above formula (15) is selected from a wide range, preferably from 1:10 to 10:1 (molar ratio). The reaction temperature is preferably −10 to 70° C. An aprotic organic solvent such as diethyl ether, tetrahydrofuran, benzene or toluene is preferably used as the solvent. The spironization of the alcohol under a neutral to acid condition is preferably carried out by using an acid catalyst such as acetic acid, hydrochloric acid, sulfuric acid, benzenesulfonic acid, p-toluenesulfonic acid or acid alumina. This acid catalyst is preferably used in an amount of 0.1 to 10 parts by weight based on 100 parts by weight of the alcohol. For this spironization, a solvent such as tetrahydrofuran, benzene or toluene is used.

The propargyl alcohol compound represented by the above formula (7) can be synthesized by various methods. For example, it can be easily synthesized by reacting a ketone compound corresponding to the above formula (7) with a metal acetylene compound such as lithium acetylide.

The chromene compound of the present invention which is synthesized as described above dissolves well in a general-purpose organic solvent such as toluene, chloroform or tetrahydrofuran. When the chromene compound represented by the above formula (1) is dissolved in such a solvent, the obtained solution is generally almost achromatic and transparent and has an excellent photochromic function that it develops a color swiftly upon exposure to sunlight or ultraviolet radiation and reversibly returns to its original achromatic state swiftly by blocking the light.

(Combination with Another Photochromic Compound>

Although the chromene compound of the present invention develops a color of a neutral tint by itself, it may be used in combination with another photochromic compound to obtain various colors required as a photochromic lens. Any known compound may be used as the photochromic compound to be combined with. Examples of the photochromic compound include fulgide, fulgimide, spirooxazine and chromene. Out of these, a chromene compound is particularly preferred because it can keep an even color at the time of color development and fading, can suppress a color drift at the time of color development due to the deterioration of photochromic properties and further can reduce initial coloration.

That is, by combining the chromene compound of the present invention with another chromene compound which has high color development sensitivity, high fading speed and little initial coloration like the above chromene compound, a photochromic composition which keeps an even color at the time of color development and fading and provides high transparency can be obtained.

To obtain a photochromic composition comprising the chromene compound of the present invention and another chromene compound, the ratio of these chromene compounds is suitably determined according to a desired color. The amount of the chromene compound of the present invention or another chromene compound is preferably 0.001 to 10 parts by mass based on 100 parts by mass of the total of all the polymerizable monomers. Stated more specifically, in the case of a thin film such as a coating film (for example, a thin film having a thickness of about 100 μm), color control should be carried out by using 0.001 to 5.0 parts by mass of the chromene compound of the present invention and 0.001 to 5.0 parts by mass of another chromene compound based on 100 parts by mass of the coating film or the total of all the polymerizable monomers which provide the coating film. In the case of a thick cured material (for example, a cured material having a thickness of 1 mm or more), color control should be carried out by using 0.001 to 0.5 part by mass of the chromene compound of the present invention and 0.001 to 0.5 part by mass of another chromene compound based on 100 parts by mass of the thick cured material or the total of all the polymerizable monomers which provide the thick cured material.

(Stabilizer to be Combined with)

Although the chromene compound of the present invention has high durability as it is, its durability can be further enhanced by using the following ultraviolet absorbent, optical stabilizer or antioxidant. As the ultraviolet absorbent may be used known ultraviolet absorbents such as benzophenone-based compounds, benzotriazole-based compounds, cyanoacrylate-based compounds, triazine-based compounds and benzoate-based compounds. Cyanoacrylate-based compounds and benzophenone-based compounds are particularly preferred. The above ultraviolet stabilizer is preferably used in an amount of 0.001 to 5 parts by mass based on 100 parts by mass of the total of all the polymerizable monomers including the chromene compound of the present invention. Known hindered amines may be used as the optical stabilizer, and known hindered phenols may be used as the antioxidant. The above optical stabilizer and the above antioxidant are each preferably used in an amount of 0.01 to 10 parts by mass based on 100 parts by mass of the total of all the polymerizable monomers including the chromene compound of the present invention.

(Use of Chromene Compound)

The chromene compound of the present invention exhibits the same photochromic properties even in a polymer solid matrix. The target polymer solid matrix is not particularly limited if the chromene compound of the present invention can be uniformly dispersed therein, and examples of the optically preferred polymer solid matrix include thermoplastic resins such as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethylmethacrylate), polydimethylsiloxane and polycarbonate.

A thermosetting resin obtained by polymerizing a radically polymerizable polyfunctional monomer may also be used as the above polymer matrix. Examples of the radically polymerizable polyfunctional monomer include polyacrylic acid esters and polymethacrylic acid esters such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl) propane and 2,2-bis(3,5-dibromo-4-methacryloyloxyethoxyphenyl)propane; polyallyl compounds such as diallyl phthalate, diallyl terephthalate, diallyl isophthalate, diallyl tartarate, diallyl epoxysuccinate, diallyl fumarate, diallyl chlorendate, diallyl hexaphthalate, diallyl carbonate, allyl diglycol carbonate and trimethylolpropane triallyl carbonate; polythioacrylic acid esters and polythiomethacrylic acid esters such as 1,2-bis(methacryloylthio)ethane, bis(2-acryloylthioethyl)ether and 1,4-bis(methacryloylthiomethyl)benzene; acrylic acid esters and methacrylic acid esters such as glycidyl acrylate, glycidyl methacrylate, β-methylglycidyl methacrylate, bisphenol A-monoglycidyl ether-methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate and 3-glycidyloxy-2-hydroxypropyloxy)-2-hydroxypropyl acrylate; and divinyl benzene.

Copolymers obtained by copolymerizing the above-described radically polymerizable polyfunctional monomers with radically polymerizable monofunctional monomers may also be used as the above polymer matrix. The radically polymerizable monofunctional monomers include unsaturated carboxylic acids such as acrylic acid, methacrylic acid and maleic anhydride; acrylic acid esters and methacrylic acid esters such as methyl acrylate, methyl methacrylate, benzyl methacrylate, phenyl methacrylate and 2-hydroxyethyl methacrylate; fumarate esters such as diethyl fumarate and diphenyl fumarate; thioacrylic acid esters and thiomethacrylic acid esters such as methyl thioacrylate, benzyl thioacrylate and benzyl thiomethacrylate; and vinyl compounds such as styrene, chlorostyrene, methyl styrene, vinyl naphthalene, α-methylstyrene dimer and bromostyrene.

As the method of dispersing the chromene compound of the present invention into the above polymer solid matrix, methods known per se may be employed. The methods include one in which the above thermoplastic resin and the chromene compound are kneaded together while they are molten to disperse the chromene compound into the resin, one in which the chromene compound is dissolved in the above polymerizable monomers and then a polymerization catalyst is added to polymerize the polymerizable monomers by heat or light so as to disperse the chromene compound into the resin, and one in which the surfaces of the above thermoplastic resin and the above thermosetting resin are dyed with the chromene compound to disperse the chromene compound into the resins.

The chromene compound of the present invention can be widely used as a photochromic material for use in, for example, recording materials as substitutes for silver halide photosensitive materials, copy materials, printing photosensitive materials, recording materials for cathode ray tubes, photosensitive materials for lasers and photosensitive materials for holography. A photochromic material comprising the chromene compound of the present invention may also be used as a photochromic lens material, optical filter material, display material or material for actinometers and ornaments.

For instance, when the chromene compound of the present invention is used in a photochromic lens, its production process is not particularly limited as long as uniform light control performance is obtained. Examples of the process include one in which a polymer film containing the photochromic material of the present invention uniformly dispersed therein is sandwiched between lenses, one in which the chromene compound of the present invention is dispersed into the above polymerizable monomers and the polymerizable monomers are polymerized by a predetermined technique, and one in which the chromene compound of the present invention is dissolved in, for example, silicone oil, the resulting solution is impregnated into the surface of a lens at 150 to 200° C. over 10 to 60 minutes, and the surface is further coated with a curable substance to obtain a photochromic lens. Further, a process in which the above polymer film is formed on the surface of a lens and the surface is coated with a curable substance to obtain a photochromic lens may also be employed.

Moreover, a photochromic lens can also be manufactured by applying a coating agent composed of a photochromic curable composition comprising the chromene compound of the present invention to the surface of a lens substrate and curing the coating film. At this point, the lens substrate may be subjected to a surface treatment with an alkaline solution or a plasma treatment in advance, and a primer may be further applied so as to improve adhesion between the substrate and the coating film by carrying out or not carrying out the above surface treatment.

EXAMPLES

The following examples are provided for the purpose of further illustrating the present invention but are in no way to be taken as limiting.

Example 1

Synthesis of Chromene Compound 1.0 g (1.9 mmol) of the following naphthol compound (18) and 0.80 g (3.0 mmol) of the following propargyl alcohol compound (19) were dissolved in 70 ml of toluene, 0.022 g of p-toluenesulfonic acid was further added to the resulting solution, and the obtained mixture was stirred under reflux by heating for 1 hour.

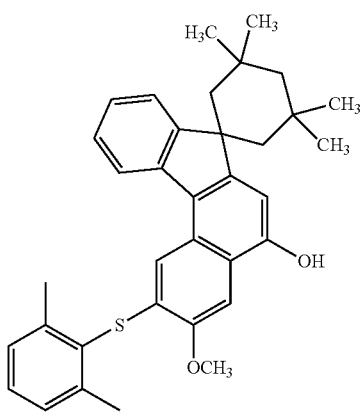

(18)

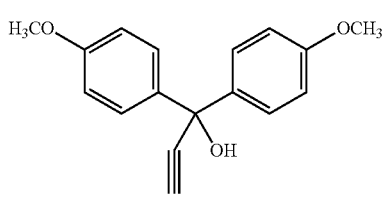

(19)

After a reaction, the solvent was removed, and the obtained product was purified on silica gel by chromatography to obtain 1.1 g of a white powdery product. The yield was 75%.

The elemental analysis values of this product were 80.72% of C, 6.80% of H and 4.13% of S which were almost equal to the calculated values of $C_{52}H_{52}O_4S$ (C, 80.79%, H, 6.78%, S, 4.15%).

When the proton nuclear magnetic resonance spectrum of the product was measured, it showed 24H peaks based on the methyl proton and methylene proton of a tetramethylcyclohexane ring and the ortho-position methyl of a thiophenyl ring at δ of around 1.0 to 3.0 ppm, a 9H peak based on the methyl proton of a methoxy group at δ of around 2.3 to 4.0 ppm and 19H peaks based on an aromatic proton and an alkene proton at δ of around 5.6 to 9.0 ppm.

Further, when the $^{13}C$-nuclear magnetic resonance spectrum was measured, it showed a peak based on the carbon of an aromatic ring at δ of around 110 to 160 ppm, a peak based on the carbon of an alkene at δ of around 80 to 140 ppm and a peak based on the carbon of an alkyl at δ of around 20 to 60 ppm.

It was confirmed from the above results that the isolated product was a chromene compound represented by the following formula (20).

The chromene compound represented by the formula (20) is designated as compound No. 1.

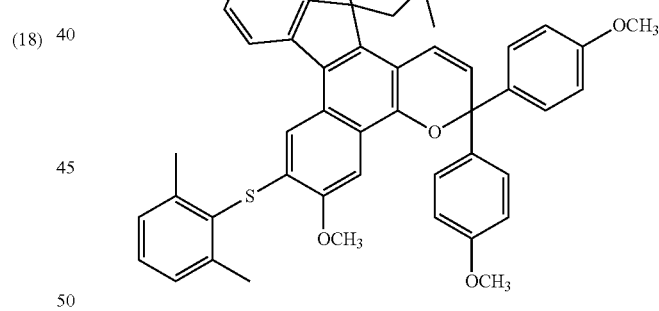

(20)

Examples 2 to 8

Synthesis of Chromene Compounds

Chromene compounds shown in Tables 3, 4 and 5 (Examples 2 to 8) were synthesized in the same manner as in Example 1. When the structures of the obtained products were analyzed by using the same structure confirming means as in Example 1, it was confirmed that they were compounds represented by structural formulas shown in Tables 3, 4 and 5. Table 6 shows the elemental analysis values, calculated values obtained from the structural formulas and characteristic $^1H$-NMR spectra of these compounds.

TABLES 3
| Example No. | Compound No. | Raw materials | |
|---|---|---|---|
| | | Naphthol compound | Propargyl alcohol compound |
| 2 | No. 2 | 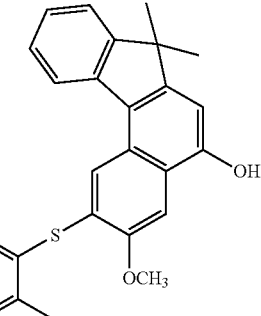 | 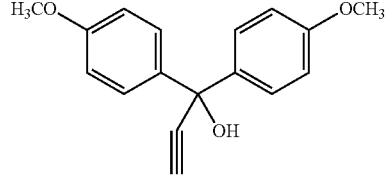 [SMILES: C#CC(O)(c1ccc(OC)cc1)c1ccc(OC)cc1] |
| 3 | No. 3 | 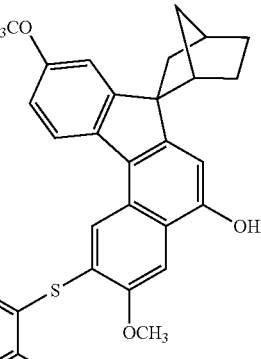 | 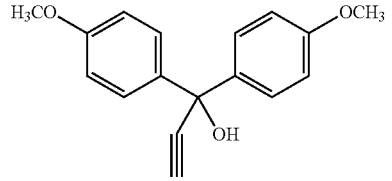 [SMILES: C#CC(O)(c1ccc(OC)cc1)c1ccc(OC)cc1] |
| 4 | No. 4 | 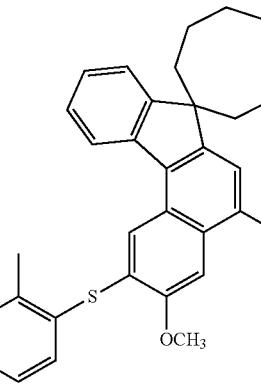 | 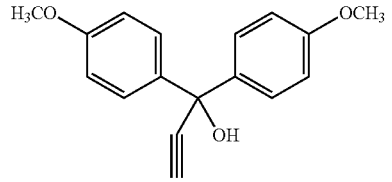 [SMILES: C#CC(O)(c1ccc(OC)cc1)c1ccc(OC)cc1] |
| Example No. | Compound No. | Product (chromen compound) | yield (%) |
|---|---|---|---|
| 2 | No. 2 | 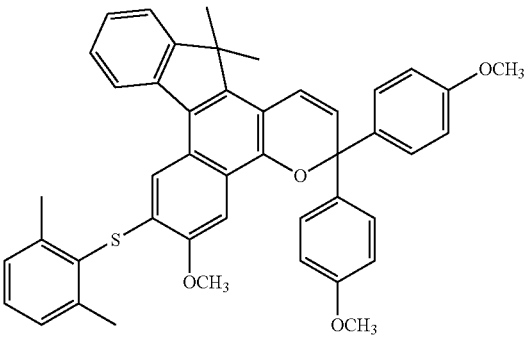 [SMILES: COc1ccc(C2(c3ccc(OC)cc3)C=Cc3c4c(c5cc(Sc6c(C)cccc6C)c(OC)cc5c3O2)-c2ccccc2C4(C)C)cc1] | 70 |

TABLES 3-continued
| | | | |
|---|---|---|---|
| 3 | No. 3 | 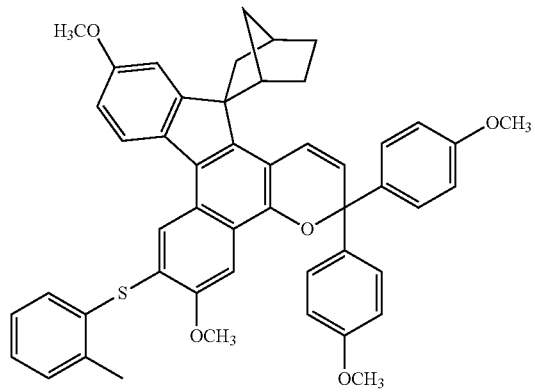 [SMILES: COc1ccc(C2(c3ccc(OC)cc3)C=Cc3c4c(c5cc(Sc6ccccc6C)c(OC)cc5c3O2)-c2ccc(OC)cc2C42CC3CCC2C3)cc1] | 62 |
| 4 | No. 4 | 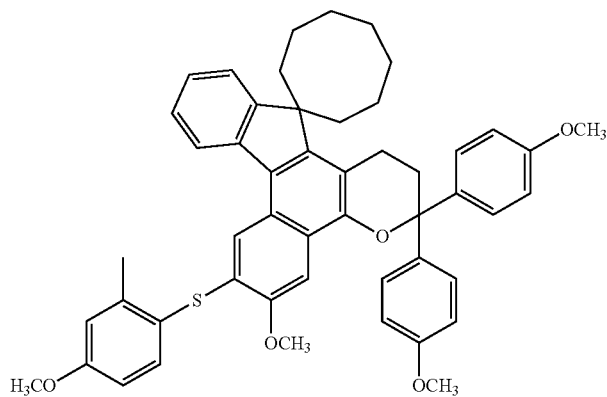 [SMILES: COc1ccc(C2(c3ccc(OC)cc3)CCc3c4c(c5cc(Sc6ccc(OC)cc6C)c(OC)cc5c3O2)-c2ccccc2C42CCCCCCC2)cc1] | 73 |
TABLE 4
| | | Raw materials | |
|---|---|---|---|
| Example No. | Compound No. | Naphthol compound | Propargyl alcohol compound |
| 5 | No. 5 | 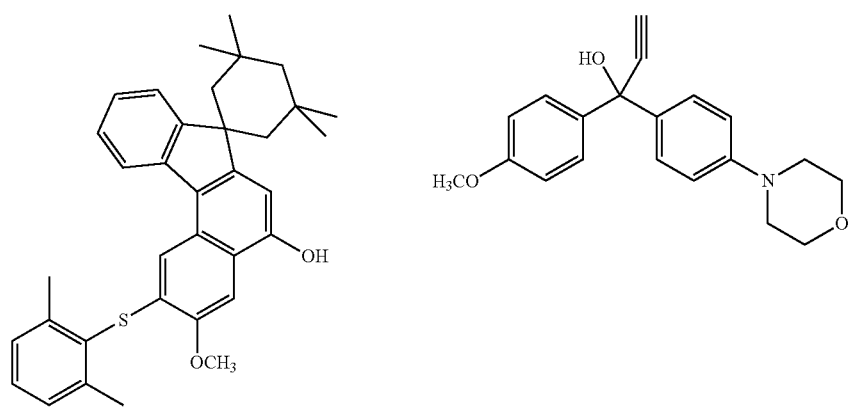 | |

TABLE 4-continued
| | | | |
|---|---|---|---|
| 6 | No. 6 | 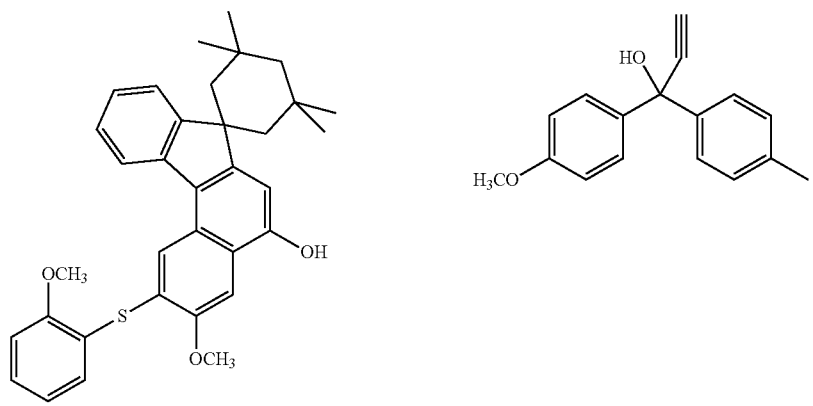 | |
| Example No. | Compound No. | Product (chromen compound) | yield (%) |
|---|---|---|---|
| 5 | No. 5 | 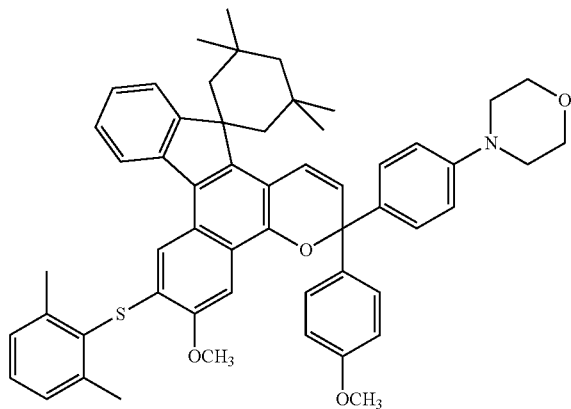 [SMILES: COc1ccc(C2(c3ccc(N4CCOCC4)cc3)C=Cc3c4c(c5cc(Sc6c(C)cccc6C)c(OC)cc5c3O2)-c2ccccc2C42CC(C)(C)CC(C)(C)C2)cc1] | 72 |
| 6 | No. 6 | 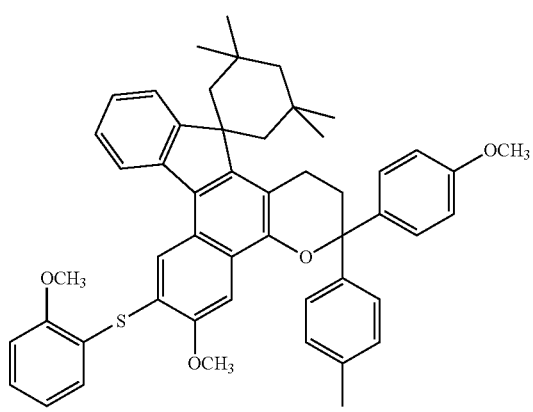 [SMILES: COc1ccc(C2(c3ccc(C)cc3)CCc3c4c(c5cc(Sc6ccccc6OC)c(OC)cc5c3O2)-c2ccccc2C42CC(C)(C)CC(C)(C)C2)cc1] | 72 |

TABLE 5
| Example No. | Compound No. | Raw materials | |
|---|---|---|---|
| | | Naphthol compound | Propargyl alcohol compound |
| 7 | No. 7 | 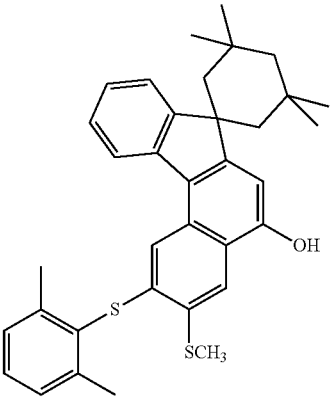 [SMILES: CSc1cc2c(O)cc3c(c2cc1Sc1c(C)cccc1C)-c1ccccc1C31CC(C)(C)CC(C)(C)C1] | 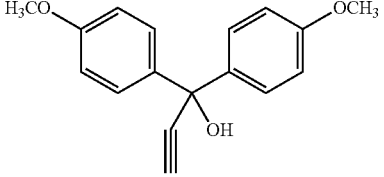 [SMILES: C#CC(O)(c1ccc(OC)cc1)c1ccc(OC)cc1] |
| 8 | No. 8 | 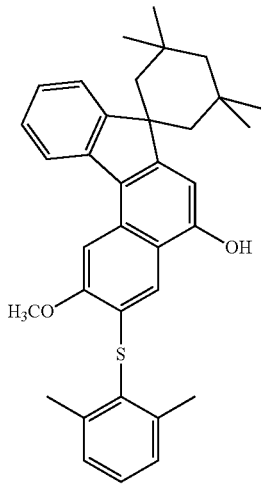 [SMILES: COc1cc2c3c(cc(O)c2cc1Sc1c(C)cccc1C)C1(CC(C)(C)CC(C)(C)C1)c1ccccc1-3] | 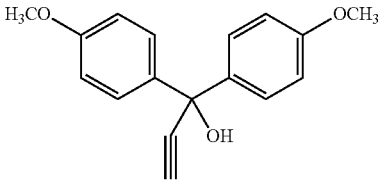 [SMILES: C#CC(O)(c1ccc(OC)cc1)c1ccc(OC)cc1] |
| Example No. | Compound No. | Product (chromen compound) | yield (%) |
|---|---|---|---|
| 7 | No. 7 | 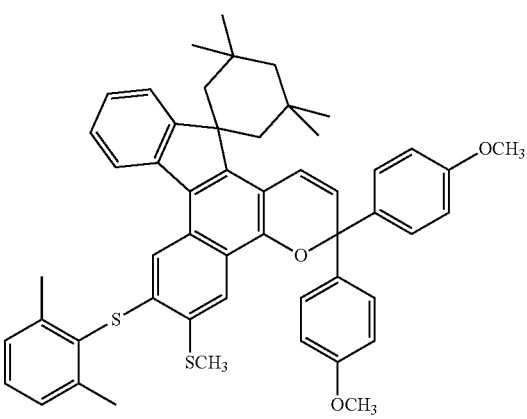 [SMILES: COc1ccc(C2(c3ccc(OC)cc3)C=Cc3c4c(c5cc(Sc6c(C)cccc6C)c(SC)cc5c3O2)-c2ccccc2C42CC(C)(C)CC(C)(C)C2)cc1] | 75 |

TABLE 5-continued

| 8 | No. 8 | 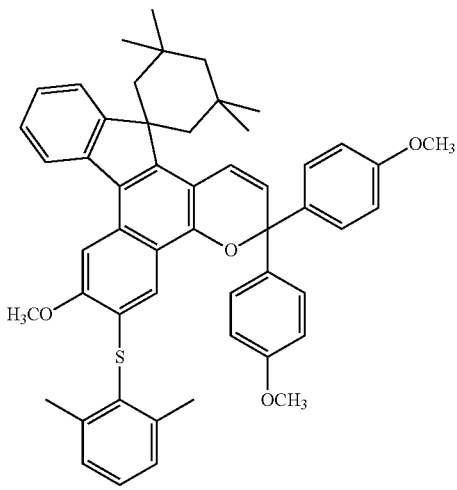 [SMILES: COc1ccc(C2(c3ccc(OC)cc3)C=Cc3c4c(c5cc(OC)c(Sc6c(C)cccc6C)cc5c3O2)-c2ccccc2C42CC(C)(C)CC(C)(C)C2)cc1] | 72 |

TABLE 6

| Example No. | Compound No. | Experimental values | | | | Calculated values | | | | 1H-NMR(ppm) |
|---|---|---|---|---|---|---|---|---|---|---|
| | | C | H | N | S | C | H | N | S | |
| 1 | No. 1 | 80.79 | 6.78 | | 4.15 | 80.45 | 6.63 | | 4.29 | δ5.5-9.0 19H |
| | | | | | | | | | | δ0.5-4.5 33H |
| 2 | No. 2 | 79.85 | 5.96 | | 4.74 | 79.51 | 6.02 | | 4.79 | δ5.5-9.0 19H |
| | | | | | | | | | | δ0.5-4.5 21H |
| 3 | No. 3 | 79.21 | 6.08 | | 4.40 | 79.00 | 5.95 | | 4.30 | δ5.5-9.0 19H |
| | | | | | | | | | | δ0.5-4.5 25H |
| 4 | No. 4 | 79.00 | 6.49 | | 4.30 | 78.92 | 6.36 | | 4.21 | δ5.5-9.0 19H |
| | | | | | | | | | | δ0.5-4.5 29H |
| 5 | No. 5 | 79.77 | 6.93 | 1.69 | 3.88 | 79.77 | 6.94 | 1.69 | 3.87 | δ5.5-9.0 19H |
| | | | | | | | | | | δ0.5-4.5 38H |
| 6 | No. 6 | 80.75 | 6.92 | | 4.24 | 80.79 | 6.78 | | 4.15 | δ5.5-9.0 19H |
| | | | | | | | | | | δ0.5-4.5 30H |
| 7 | No. 7 | 79.15 | 6.64 | | 8.13 | 79.01 | 6.63 | | 8.10 | δ5.5-9.0 19H |
| | | | | | | | | | | δ0.5-4.5 33H |
| 8 | No. 8 | 80.79 | 6.78 | | 4.15 | 80.66 | 6.75 | | 4.21 | δ5.5-9.0 19H |
| | | | | | | | | | | δ0.5-4.5 33H |

Ex.: Example

Examples 9 to 16

Evaluation of Physical Properties of Photochromic Plastic Lenses Manufactured by Coating Method The chromene compound No. 1 obtained in the above Example 1 was mixed with a photopolymerization initiator and polymerizable monomers, the resulting mixture was applied to the surface of a lens substrate, and ultraviolet light was applied to polymerize the coating film on the surface of the lens substrate.

As for the photochromic curable composition, a mixture of 50 parts by mass of 2,2-bis(4-methacryloyloxypentaethoxyphenyl)propane, 10 parts by mass of polyethylene glycol diacrylate (average molecular weight of 532), 10 parts by mass of trimethylolpropane trimethacrylate, 10 parts by mass of polyester oligomer hexaacrylate (EB-1830 of Daicel UCB Co., Ltd.) and 10 parts by mass of glycidyl methacrylate as radically polymerizable monomers was used. After 1 part by mass of the chromene compound No. 1 obtained in Example 1 was added to and fully mixed with 90 parts by mass of the mixture of these radically polymerizable monomers, 0.3 part by mass of CGI1800 {a mixture of 1-hydroxycyclohexylphenyl ketone and bis(2,6-dimethoxybenzoyl)-2,4,4-trimethylpentylphosphine oxide (weight ratio of 3:1)} as a photopolymerization initiator, 5 parts by mass of bis(1,2,2,6,6-pentamethyl-4-piperidyl)sebacate and 3 parts by mass of ethylenebis(oxyethylene)bis[3-(5-tert-butyl-4-hydroxy-m-tolyl)propionate] as a stabilizer, 7 parts by mass of γ-methacryloyloxypropyl trimethoxysilane as a silane coupling agent, and 3 parts by mass of N-methyldiethanolamine were added to and fully mixed with the above mixture to obtain a photochromic curable composition.

Subsequently, about 2 g of the photochromic curable composition obtained by the above method was applied to the surface of a lens substrate (CR39: allyl resin plastic lens; refractive index of 1.50) by using the 1H-DX2 spin coater of MIKASA Co., Ltd. This coated lens was irradiated with light from a metal halide lamp having an output of 120 mW/cm$^2$ in a nitrogen gas atmosphere for 3 minutes to cure the photochromic curable composition so as to manufacture an optical article (photochromic plastic lens) which was covered with a polymer film containing the chromene compound dispersed therein (thickness of polymer film: 40 μm).

The following photochromic properties of the obtained photochromic plastic lens were evaluated. The evaluation results obtained by using the chromene compound of Example 1 are shown in Table 7. The following evaluations were carried out at a room temperature of 23° C.

[1] Maximum absorption wavelength ($\lambda_{max}$): This is the maximum absorption wavelength after color development obtained by means of the spectrophotometer (MCPD3000 instantaneous multi-channel photodetector) of Otsuka Electronics Co., Ltd. and used as an index of color at the time of color development.

[2] Color optical density ($A_0$): This is the difference between absorbance {$\epsilon(120)$} after 120 seconds of exposure at the above maximum absorption wavelength and absorbance $\epsilon(0)$ under no exposure and used as an index of color optical density. It can be said that as this value becomes larger, photochromic properties become better.

[3] Double peak characteristic ($A_Y/A_B$): This is the ratio of color optical density ($A_Y$:value of $\lambda_{max}$) at a yellow range (having a maximum absorption wavelength at 430 to 530 nm) and color optical density ($A_B$:value of $\lambda_{max}$) at a blue range (having a maximum absorption wavelength at 550 to 650 nm) and used as an index of double peak characteristic.

[4] Fading half period [$\tau\frac{1}{2}$(sec.)]: This is a time required for the reduction of the absorbance at the above maximum absorption wavelength of a sample to ½ of {$\epsilon(120)-\epsilon(0)$} when exposure is stopped after 120 seconds of exposure and used as an index of fading speed. As this time becomes shorter, the fading speed becomes higher.

[5] Absorption end {$\lambda_0$}: After the photochromic plastic lens obtained under the above conditions is used as a sample and kept in the dark for one day, the ultraviolet light transmittance (T %) at 300 to 800 nm of the sample is measured with an ultraviolet visible spectrophotometer (UV-2550 of Shimadzu Corporation) at room temperature. A tangent line is drawn on the obtained ultraviolet light absorption curve to ensure that the transmittance (T %) of the ultraviolet light absorption curve passes a point of 50% so as to obtain an absorption wavelength at which the transmittance (T %) of the tangent line becomes 0 as the absorption end (absorption end of the ultraviolet light spectrum) and used as an index of initial coloration. For example, in an optical article such as a spectacle lens, as this value becomes smaller, initial coloration becomes weaker and transparency under no exposure becomes higher.

[6] Residual rate ($A_{50}/A_0 \times 100$): A deterioration promotion test was made on the obtained photochromic plastic lens by using the X25 xenon weather meter of Suga Test Instruments Co., Ltd. for 50 hours. Thereafter, the above color optical density is evaluated before and after the test by measuring the color optical density ($A_0$) before the test and the color optical density ($A_{50}$) after the test in order to obtain the ratio ($A_{50}/A_0$) of these values as residual rate which is used as an index of color development durability. As the residual rate becomes higher, color development durability becomes higher.

[7] heat resistance test ($\Delta YI$ and color drift): A heating test is conducted on the obtained photochromic plastic lens at 110° C. for 12 hour to measure the yellowness index and color drift of the lens. The measurement methods are described below.

[7-1] yellowness index ($\Delta YI$): The yellowness index (YI) before color development of the lens sample is evaluated before and after the heating test. The color difference meter (SM-4) of Suga Test Instruments Co., Ltd. is used for this measurement. As the difference ($\Delta YI = YI_{after} - YI_{before}$) between YI ($YI_{after}$) after the test and YI ($YI_{before}$) before the test is larger, the yellowness index after the test becomes larger.

[7-2] color drift {$1-(A'_Y/A'_B)/(A_Y/A_B)$}: The double peak characteristic shown in [3] is measured before the heating test ($A_Y/A_B$) and after the heating test ($A'_Y/A'_B$). As for a color drift by the heating test, as the color drift value {color drift=$1-(A'_Y/A'_B)/(A_Y/A_B)$} is larger, a change in developed hue by the heating test becomes larger, which means that a color drift becomes larger.

Photochromic plastic lenses were obtained and their characteristic properties were evaluated in the same manner as described above except that the compounds obtained in Examples 2 to 8 (Nos. 2 to 8) were used as chromene compounds. The results are shown in Table 7.

TABLE 7

| | Compound No. | Maximum absorption wavelength λmax (nm) | Color optical density $A_0$ | Double peak characteristic $A_Y/A_B$ | Fading half period τ½ (sec) | Absorption end $\lambda_0$ (nm) | Residual rate ($A_{50}/A_0$) × 100(%) | Heat resistance | |
|---|---|---|---|---|---|---|---|---|---|
| | | | | | | | | ΔYI | $1-(A'_Y/A'_B)/(A_Y/A_B)$ |
| Ex. 9 | No. 1 | 461 | 0.77 | 1.33 | 40 | 410 | 89 | 1 | 0 |
| | | 570 | 0.58 | | 40 | | 88 | | |
| Ex. 10 | No. 2 | 465 | 0.64 | 1.39 | 110 | 411 | 88 | 1.2 | 0.02 |
| | | 576 | 0.46 | | 111 | | 88 | | |
| Ex. 11 | No. 3 | 458 | 0.46 | 1.35 | 43 | 410 | 86 | 1.6 | 0.05 |
| | | 577 | 0.34 | | 44 | | 86 | | |
| Ex. 12 | No. 4 | 462 | 0.87 | 1.47 | 88 | 409 | 89 | 1.5 | 0.01 |
| | | 573 | 0.59 | | 87 | | 88 | | |
| Ex. 13 | No. 5 | 481 | 0.59 | 1.04 | 35 | 409 | 87 | 1 | 0 |
| | | 588 | 0.57 | | 34 | | 86 | | |
| Ex. 14 | No. 6 | 450 | 0.76 | 1.69 | 90 | 411 | 80 | 1.7 | 0.08 |
| | | 568 | 0.45 | | 89 | | 79 | | |
| Ex. 15 | No. 7 | 450 | 0.79 | 1.41 | 44 | 412 | 86 | 1.1 | 0.02 |
| | | 564 | 0.56 | | 45 | | 86 | | |
| Ex. 16 | No. 8 | 460 | 0.76 | 1.33 | 42 | 400 | 84 | 0.5 | 0.03 |
| | | 569 | 0.57 | | 41 | | 85 | | |

Ex.: Example

Comparative Examples 1 to 4

For comparison, photochromic plastic lenses were obtained and their characteristic properties were evaluated in the same manner as in Examples except that compounds represented by the following formulas (A), (B), (C) and (D) were used. The results are shown in Table 8.

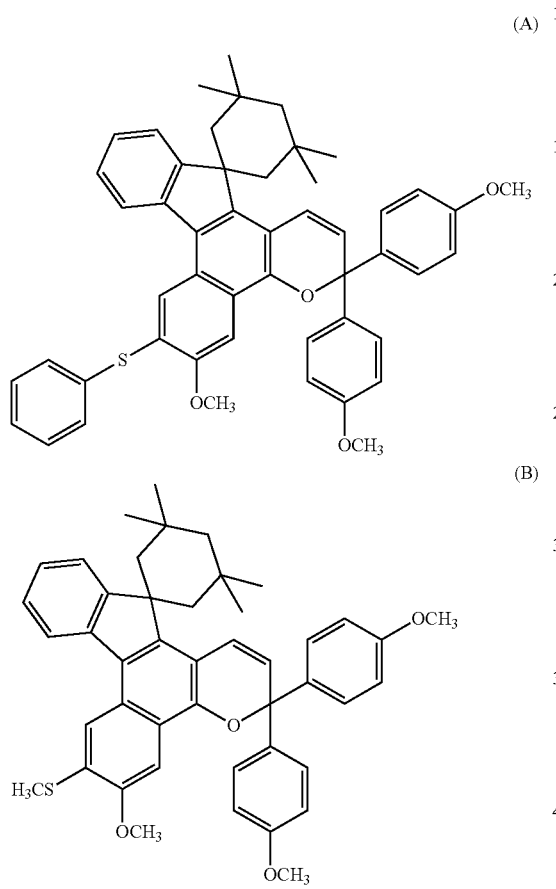

(A)

(B)

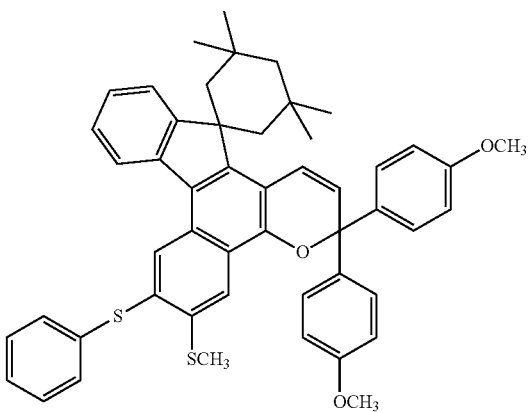

(C)

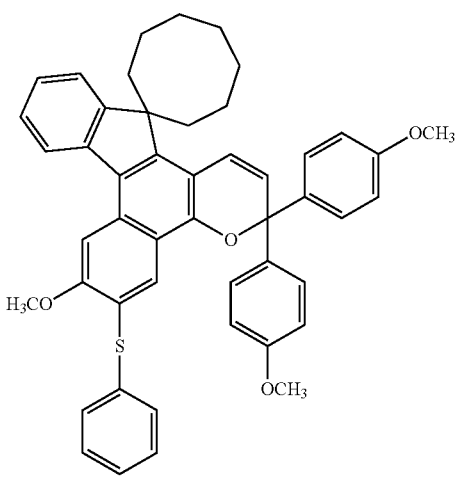

(D)

TABLE 8

| Compound No. | λmax (nm) | Color optical density $A_0$ | Double peak characteristic $A_Y/A_B$ | Fading half period $\tau^{1/2}$ (sec) | Absorption end $\lambda_0$ (nm) | Residual rate $(A_{50}/A_0) \times 100(\%)$ | Heat resistance ΔYI | $1-(A'_Y/A'_B)/(A_Y/A_B)$ |
|---|---|---|---|---|---|---|---|---|
| Com. Ex. 1  A | 461 | 0.75 | 1.32 | 62 | 410 | 75 | 3.3 | 0.18 |
|  | 570 | 0.57 |  | 63 |  | 77 |  |  |
| Com. Ex. 2  B | 464 | 0.51 | 1.50 | 50 | 411 | 82 | 3.7 | 0.17 |
|  | 573 | 0.34 |  | 50 |  | 82 |  |  |
| Com. Ex. 3  C | 481 | 0.63 | 1.54 | 69 | 413 | 87 | 3.5 | 0.2 |
|  | 580 | 0.41 |  | 69 |  | 87 |  |  |
| Com. Ex. 4  D | 462 | 0.85 | 1.35 | 90 | 400 | 79 | 2.2 | 0.25 |
|  | 573 | 0.63 |  | 90 |  | 78 |  |  |

Com. Ex.: Comparative Example

It is understood that the photochromic plastic lenses of Examples 9 to 16 obtained by using the chromene compounds of the present invention were superior in fading speed and durability to the photochromic plastic lenses of Comparative Example 1 (chromene compound represented by the above formula (A)), Comparative Example 2 (chromene compound represented by the above formula (B)), Comparative Example 3 (chromene compound represented by the above formula (C)) and Comparative Example 4 (chromene compound represented by the above formula (D)) while having high heat resistance.

Example 17

Production of Naphthol Compound 60.6 g (324.2 mmol) of 2-bromoanisole was added dropwise to a dichloromethane solution (350 ml) containing 51.8 g (388.6 mmol) of aluminum chloride and 45.6 g (324.3 mmol) of benzoyl chloride which was cooled to 0° C. After addition, the resulting mixture was stirred for 2 hours. After a reaction, the reaction solution was washed with water, the solvent was removed, and the obtained product was purified by column chromatography to obtain a benzophenone derivative represented by the following formula (21) as 61.3 g (210.7 mmol, yield of 75%) of a yellow solid.

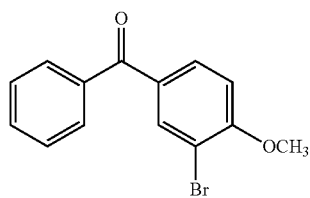
(21)

The benzophenone derivative of the above formula (21), 30.0 g (232.0 mmol) of N-ethyl-N,N-diisopropylamine, 3.91 g (4.2 mmol) of tris(dibenzylideneacetone)dipalladium, 4.7 g (8.4 mmol) of 1,1'-bis(diphenylphosphino)ferrocene and 29.1 g (210.7 mmol) of 2,6-dimethylthiobenzene were dissolved in 650 ml of toluene in an argon atmosphere and refluxed for 3 hours. After a reaction, the reaction solution was washed with water, the solvent was removed, and the obtained product was purified by column chromatography to obtain a benzophenone derivative represented by the following formula (22) as 69.7 g (200.0 mmol, yield of 95%) of a yellow solid.

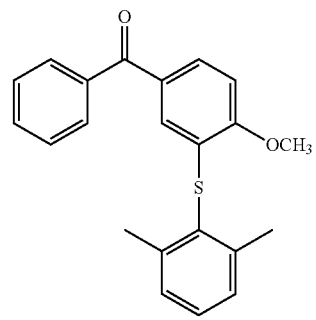
(22)

The benzophenone derivative of the above formula (22) and 46.2 g (265.0 mmol) of diethyl succinate were dissolved in 250 ml of tetrahydrofuran and heated at 55° C. A tetrahydrofuran solution (250 ml) containing 29.7 g (265.0 mmol) of potassium-t-butoxide was added dropwise to this solution and stirred for 1 hour. After a reaction, the resulting reaction solution was washed with concentrated hydrochloric acid and then with water, and the solvent was removed to obtain a compound represented by the following formula (23) as 95.3 g (200.0 mmol, yield of 100%) of orange oil.

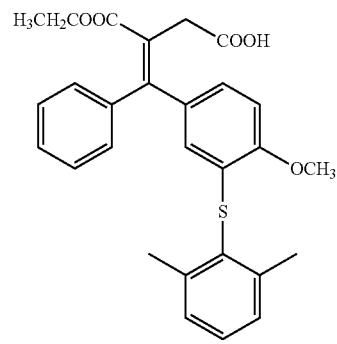
(23)

The above compound of the formula (23), 16.4 g (200.0 mmol) of sodium acetate and 102.9 g (1,000.0 mmol) of acetic anhydride were dissolved in 300 ml of toluene and refluxed for 3 hours. After a reaction, the reaction solution was washed with water, the solvent was removed, and the obtained product was purified by recrystallization with methanol so as to obtain a compound represented by the following formula (24) as 21.0 g (42.0 mmol, yield of 21%) of an orange solid.

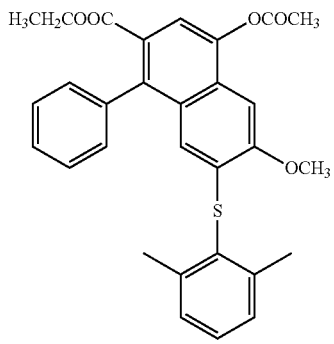

(24)

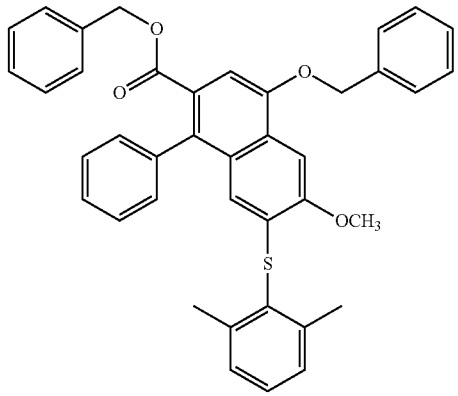

(26)

The above compound of the formula (24) was dispersed into 100 ml of methanol. 127 ml of an aqueous solution containing 25.2 g (630.0 mmol) of sodium hydroxide was added to this dispersion and refluxed for 3 hours. After a reaction, the reaction solution was washed with concentrated hydrochloric acid and then with water, the solvent was removed, and the obtained product was purified by reslurrying with toluene to obtain a carboxylic acid derivative represented by the following formula (25) as 16.6 g (38.6 mmol, yield of 92%) of a yellow solid.

The above compound of the formula (26) was dispersed into 400 ml of isopropyl alcohol. 150 ml of an aqueous solution containing 30.0 g (750.0 mmol) of sodium hydroxide was added to this dispersion and refluxed for 3 hours. After a reaction, the reaction solution was washed with concentrated hydrochloric acid and then with water, the solvent was removed, and the obtained product was purified by reslurrying with toluene to obtain a carboxylic acid derivative represented by the following formula (27) as 17.5 g (33.7 mmol, yield of 97%) of a yellow solid.

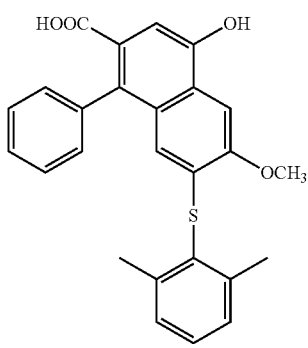

(25)

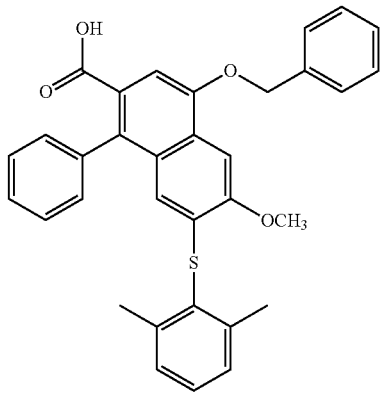

(27)

The above compound of the formula (25) and 14.8 g (107.4 mmol) of benzyl chloride were dissolved in 150 ml of N,N-dimethylformamide. 15.4 g (122.0 mmol) of potassium carbonate was added to this solution, and the resulting mixture was heated at 60° C. and stirred for 3 hours. After a reaction, the resulting reaction solution was washed with water, and the solvent was removed to obtain a compound represented by the following formula (26) as 21.2 g (34.7 mmol, yield of 90%) of yellow oil.

The above compound of the formula (27) was dispersed into 300 ml of toluene. 90.0 g (891.1 mmol) of triethylamine and 15.9 g (57.9 mmol) of diphenylphosphorylazide were added to this dispersion and stirred at room temperature for 2 hours. 20.0 g (435.3 mmol) of ethanol was added to this solution to carry out a reaction at 70° C. for 2 hours. 500 ml of ethanol was added to this solution, and then 74.7 g (1335.0 mmol) of potassium hydroxide was added and refluxed for 6 hours. After a reaction, ethanol was distilled off at normal pressure, tetrahydrofuran was added, the reaction solution was washed with water, and the solvent was removed to obtain a compound represented by the following formula (28) as 14.6 g (29.7 mmol, yield of 88%) of a yellow solid.

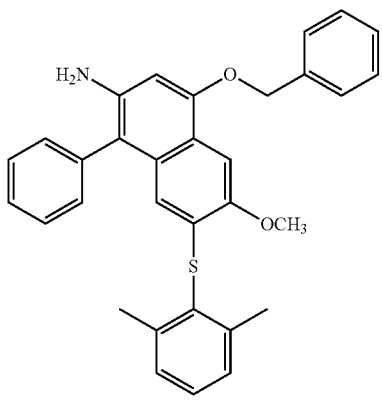

(28)

(30)

The above compound of the formula (28) was dispersed into 350 ml of acetonitrile, and 113.7 g (187.1 mmol) of a 6% hydrochloric acid aqueous solution was added and cooled to 0 to 5° C. 11.7 g (56.7 mmol) of a 33% sodium nitrite aqueous solution was added to this solution and stirred for 30 minutes. 47.1 g (283.5 mmol) of a 50% potassium iodide aqueous solution was added to this solution and stirred at room temperature for 5 hours. After a reaction, toluene was added, the reaction solution was washed with water, the solvent was removed, and the obtained product was purified by column chromatography to obtain a compound represented by the following formula (29) as 14.3 g (23.8 mmol, yield of 80%) of a yellow solid.

The above compound of the formula (30) and 221.1 mg (0.9 mmol) of (±)-10-camphorsulfonic acid were dissolved in 150 ml of toluene and refluxed for 30 minutes. After the obtained solution was left to be cooled to room temperature, this solution was added to 100 ml of a toluene solution containing 4.5 g (27.3 mmol) of p-toluenesulfonic acid heated at 90° C. and refluxed for 4 hours. After a reaction, the reaction solution was washed with water, the solvent was removed, and the obtained product was purified by column chromatography to obtain a naphthol compound represented by the following formula (31) as 3.6 g (6.8 mmol, yield of 45%) of a yellow solid.

(29)

(31)

The above compound of the formula (29) was dispersed into 600 ml of toluene and cooled to −30° C. 28.1 ml (44.9 mmol) of n-butyl lithium (1.6 M hexane solution) was added dropwise to this dispersion and stirred for 30 minutes. 14.8 g of a toluene solution containing 7.4 g (47.8 mmol) of 3,3,5,5-tetramethylcyclohexanone was added dropwise to this solution and stirred at 0° C. for 3 hours. After a reaction, toluene was added, the reaction solution was washed with water, the solvent was removed, and the obtained product was purified by reslurrying with methanol to obtain a compound represented by the following formula (30) as 9.5 g (15.0 mmol, yield of 63%) of a yellow solid.

The elemental analysis values of this product were 80.51% of C, 7.21% of H and 6.20% of S which were almost equal to the calculated values of $C_{35}H_{38}O_2S$ (C, 80.42%, H, 7.33%, S, 6.13%).

When the proton nuclear magnetic resonance spectrum of the product was measured, it showed 27H peaks based on a methoxy group and an alkyl group at δ of around 0.5 to 4.5 ppm and a 10H peak based on an aromatic proton at δ of around 5.0 to 9.0 ppm.

Further, when the $^{13}$C-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (31).

This compound is the naphthol compound used in the above Example 1.

Example 18

Production of Naphthol Compound

After 8.7 g (357.06 mmol) of Mg and a small amount of iodine were dissolved in 200 ml of THF, 71.9 g (324.6 mmol) of 5-bromo-2-chloroanisole dissolved in 500 ml of THF was added dropwise to the resulting solution. After addition, the resulting mixture was refluxed for 3 hours to prepare a Grignard reagent which was then cooled to room temperature. After that, the prepared Grignard reagent was added dropwise to 50.2 g (357.06 mmol) of benzoyl chloride and stirred for 5 hours. After a reaction, the reaction solution was washed with water, the solvent was removed, and the obtained product was purified by column chromatography to obtain a benzophenone derivative represented by the following formula (32) as 32.0 g (129.8 mmol, yield of 40%) of a white solid.

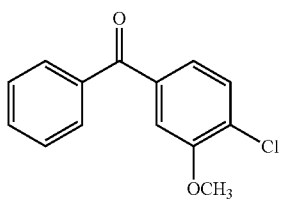

(32)

The above compound of the formula (32), 13.7 g (142.8 mmol) of sodium-t-butoxide, 0.7 g (1.3 mmol) of bis(dibenzylideneacetone)palladium, 1.75 g (1.3 mmol) of 1-dicyclohexylphosphino-2-di-t-butylphosphinoethyl ferrocene and 17.9 g (129.8 mmol) of 2,6-dimethylthiobenzene were dissolved in 400 ml of toluene in an argon atmosphere and refluxed for 3 hours. After a reaction, the reaction solution was washed with water, the solvent was removed, and the obtained product was purified by column chromatography to obtain a benzophenone derivative represented by the following formula (33) as 41.1 g (118.1 mmol, yield of 91%) of a white solid.

(33)

When the operation of Example 17 was repeated by using the benzophenone derivative of the above formula (33), a naphthol compound represented by the following formula (34) was obtained as 2.0 g (3.9 mmol, yield of 3%) of a yellow solid.

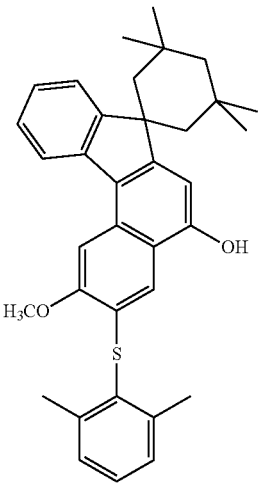

(34)

The elemental analysis values of this product were 80.38% of C, 7.30% of H and 6.10% of S which were almost equal to the calculated values of $C_{35}H_{33}O_2S$ (C, 80.42%, H, 7.33%, S, 6.13%).

When the proton nuclear magnetic resonance spectrum of the product was measured, it showed 27H peaks based on a methoxy group and an alkyl group at δ of around 0.5 to 4.5 ppm and a 10H peak based on an aromatic proton at δ of around 5.0 to 9.0 ppm.

Further, when the $^{13}$C-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (34).

This compound is a naphthol compound used in the above Example 8.

Example 19

Production of Naphthol Compound 51.3 g (300 mmol) of m-bromomethylthiobenzene was added dropwise to a dichloromethane (350 ml) solution containing 47.9 g (359.6 mmol) of aluminum chloride and 42.4 g (300 mmol) of benzoyl chloride which was cooled to 0° C. After addition, the resulting mixture was stirred for 2 hours. After a reaction, the reaction solution was washed with water, the solvent was removed, and the obtained product was purified by column chromatography to obtain a benzophenone derivative represented by the following formula (35) as 58.1 g (189 mmol, yield of 63%) of a yellow solid.

naphthol compound represented by the following formula (37) was obtained as 1.6 g (3.0 mmol, yield of 3.1%) of a yellow solid.

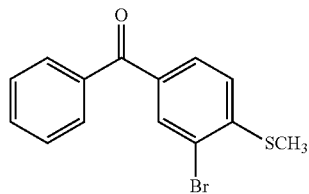

(35)

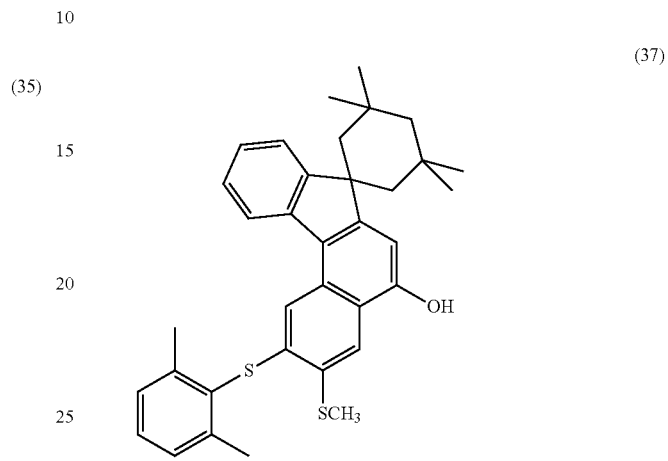

(37)

56.9 g (185 mmol) of the above benzophenone derivative of the formula (35), 51.5 g (370 mmol) of N-ethyl-N,N-diisopropylamine, 1.7 g (1.9 mmol) of tris(dibenzylideneacetone)dipalladium, 2.1 g (3.7 mmol) of 1,1'-bis(diphenylphosphino)ferrocene and 28.1 g (203.5 mmol) of 2,6-dimethylthiobenzene were dissolved in 850 ml of toluene in an argon atmosphere and refluxed for 3 hours. After a reaction, the reaction solution was washed with water, the solvent was removed, and the obtained product was purified by column chromatography to obtain a benzophenone derivative represented by the following formula (36) as 60.7 g (166.5 mmol, yield of 90%) of a yellow solid.

The elemental analysis values of this product were 78.02% of C, 7.11% of H and 11.9% of S which were almost equal to the calculated values of $C_{35}H_{38}OS_2$ (C, 78.23%, H, 7.19%, S, 11.9%).

When the proton nuclear magnetic resonance spectrum of the product was measured, it showed 28H peaks based on a methoxy group and an alkyl group at δ of around 0.5 to 4.5 ppm and a 10H peak based on an aromatic proton at δ of around 5.0 to 9.0 ppm.

Further, when the $^{13}C$-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (37).

This compound is the compound used in Example 7.

Examples 20 to 23

Production of Naphthol Compounds

Naphthol compounds shown in the table below were synthesized in the same manner as in Example 17. When the structures of the obtained products were analyzed by using the same structure confirming means as in Example 17, it was confirmed that they were naphthol compounds used in Examples shown in Tables 1 to 3. Table 9 shows the elemental analysis values, calculated values obtained from the structural formulas and characteristic $^1$H-NMR spectra of these compounds.

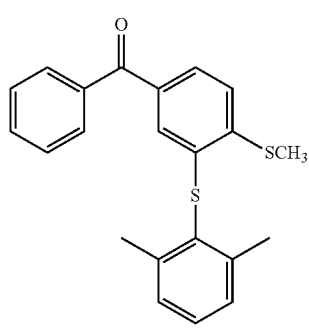

(36)

When the operation of Example 17 was repeated by using the above benzophenone derivative of the formula (36), a

TABLE 9

| Example No. | Used chromene compound No.* | Experimental values C | H | S | Calculated values C | H | S | 1H-NMR(ppm) |
|---|---|---|---|---|---|---|---|---|
| 20 | 2 | 78.75 | 6.23 | 7.43 | 78.84 | 6.14 | 7.52 | δ5.5-9.0 10H<br>δ0.5-4.5 16H |
| 21 | 3 | 77.80 | 6.15 | 6.45 | 77.70 | 6.11 | 6.48 | δ5.5-9.0 10H<br>δ0.5-4.5 20H |
| 22 | 4 | 77.75 | 6.65 | 6.40 | 77.61 | 6.71 | 6.28 | δ5.5-9.0 10H<br>δ0.5-4.5 24H |
| 23 | 6 | 77.90 | 6.93 | 6.23 | 77.83 | 6.92 | 6.11 | δ5.5-9.0 11H<br>δ0.5-4.5 25H |

*Chromene compound No. obtained by using naphthol compound

Example 24 to 46

Production of Chromene Compounds

Chromene compounds shown in Tables 10 to 15 (Examples 24 to 46) were synthesized in the same manner as in Example 1. When the structures of the obtained products were analyzed by using the same structure confirming means as in Example 1, it was confirmed that they were compounds represented by the structural formulas shown in Tables 10 to 15. Table 16 shows the elemental analysis values, calculated values obtained from the structural formulas and characteristic $^1$H-NMR spectra of these compounds.

TABLE 10

| Example No. | Compound No. | Raw materials Naphthol compound | Propargyl alcohol compound |
|---|---|---|---|
| 24 | No. 9 | 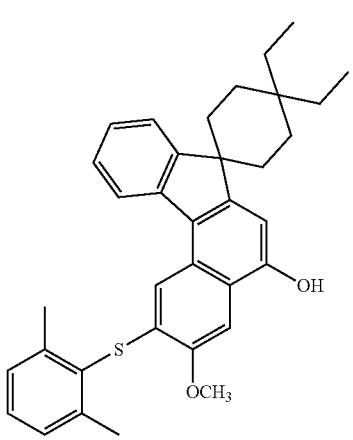 [SMILES: CCC1(CC)CCC2(CC1)c1ccccc1-c1c2cc(O)c2cc(OC)c(Sc3c(C)cccc3C)cc12] | 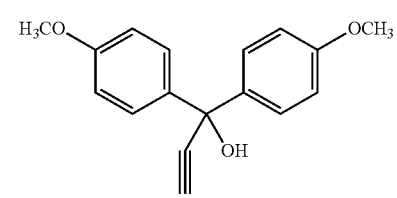 [SMILES: C#CC(O)(c1ccc(OC)cc1)c1ccc(OC)cc1] |
| 25 | No. 10 | 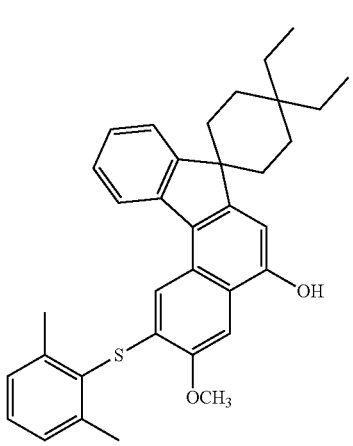 [SMILES: CCC1(CC)CCC2(CC1)c1ccccc1-c1c2cc(O)c2cc(OC)c(Sc3c(C)cccc3C)cc12] | 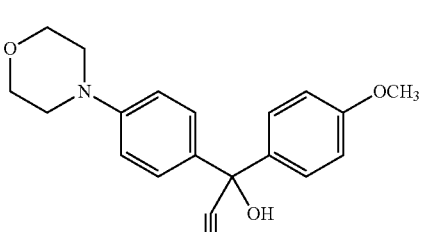 |

TABLE 10-continued
| 26 | No. 11 | 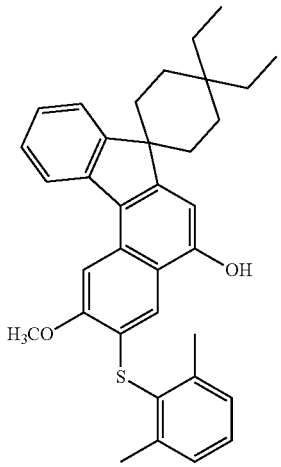 [SMILES: CCC1(CC)CCC2(CC1)c1ccccc1-c1c2cc(O)c2cc(Sc3c(C)cccc3C)c(OC)cc12] | 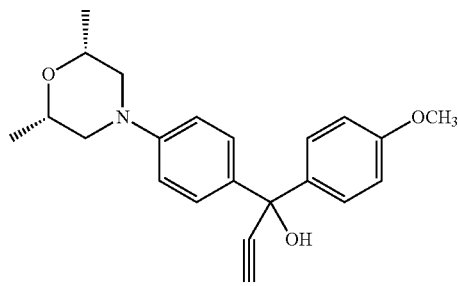 [SMILES: C#CC(O)(c1ccc(OC)cc1)c1ccc(N2C[C@@H](C)O[C@@H](C)C2)cc1] |
| 27 | No. 12 | 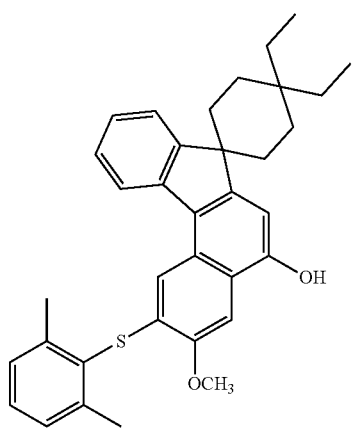 [SMILES: CCC1(CC)CCC2(CC1)c1ccccc1-c1c2cc(O)c2cc(OC)c(Sc3c(C)cccc3C)cc12] | 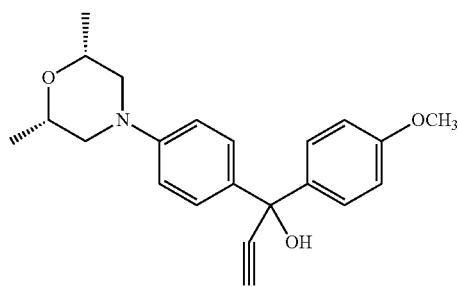 [SMILES: C#CC(O)(c1ccc(OC)cc1)c1ccc(N2C[C@@H](C)O[C@@H](C)C2)cc1] |
| Example No. | Compound No. | Product (chromene compound) | Yield (%) |
|---|---|---|---|
| 24 | No. 9 | 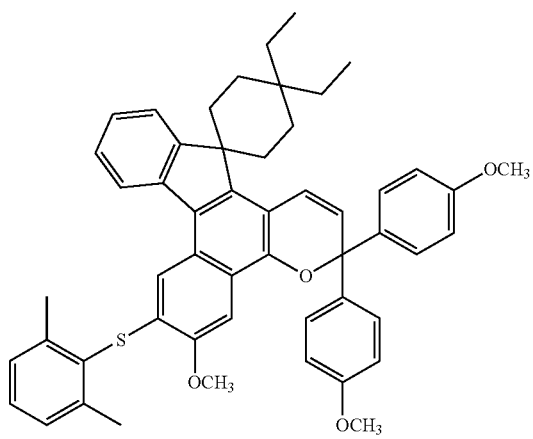 [SMILES: CCC1(CC)CCC2(CC1)c1ccccc1-c1c2c2c(c3cc(OC)c(Sc4c(C)cccc4C)cc13)OC(c1ccc(OC)cc1)(c1ccc(OC)cc1)C=C2] | 77 |

TABLE 10-continued
| 25 | No. 10 | 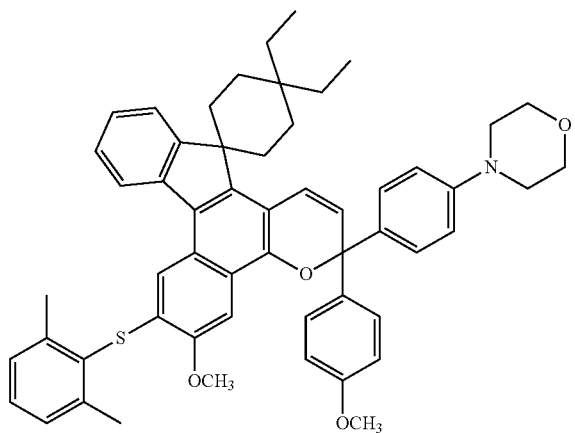 [SMILES: CCC1(CC)CCC2(CC1)c1ccccc1-c1c2c2c(c3cc(OC)c(Sc4c(C)cccc4C)cc13)OC(c1ccc(OC)cc1)(c1ccc(N3CCOCC3)cc1)C=C2] | 75 |
|---|---|---|---|
| 26 | No. 11 | 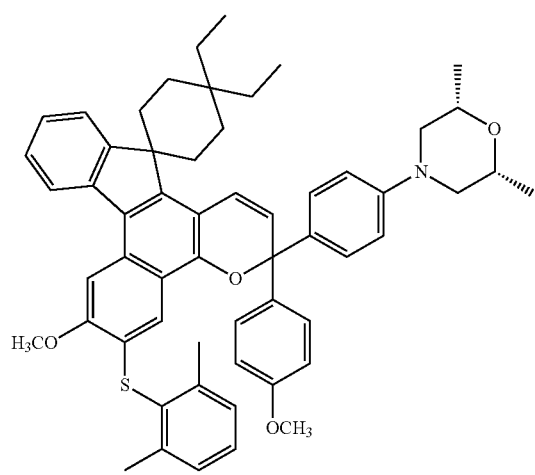 [SMILES: CCC1(CC)CCC2(CC1)c1ccccc1-c1c2c2c(c3cc(Sc4c(C)cccc4C)c(OC)cc13)OC(c1ccc(OC)cc1)(c1ccc(N3C[C@@H](C)O[C@@H](C)C3)cc1)C=C2] | 70 |
| 27 | No. 12 | 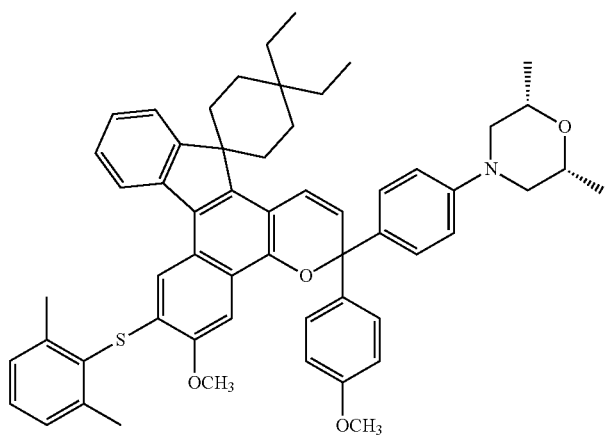 [SMILES: CCC1(CC)CCC2(CC1)c1ccccc1-c1c2c2c(c3cc(OC)c(Sc4c(C)cccc4C)cc13)OC(c1ccc(OC)cc1)(c1ccc(N3C[C@@H](C)O[C@@H](C)C3)cc1)C=C2] | 73 |
Ex.: Example TABLE 11
| Ex. No. | Compound No. | Raw materials | |
|---|---|---|---|
| | | Naphthol compound | Propargyl alcohol compound |
| 28 | No. 13 | 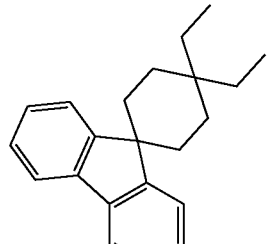 | 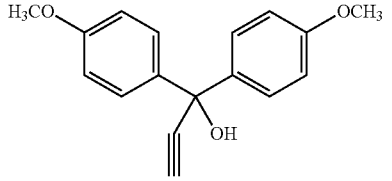 [SMILES: C#CC(O)(c1ccc(OC)cc1)c1ccc(OC)cc1] |
| 29 | No. 14 | 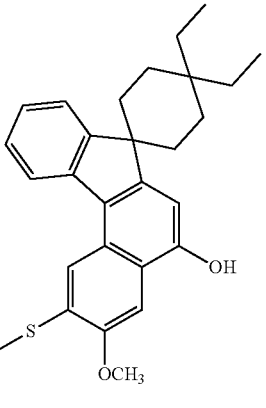 | 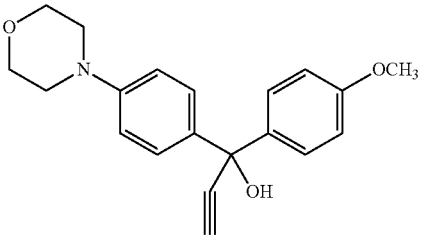 [SMILES: C#CC(O)(c1ccc(OC)cc1)c1ccc(N2CCOCC2)cc1] |
| 30 | No. 15 | 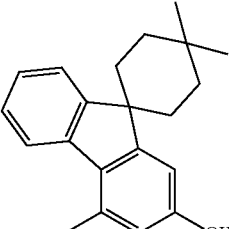 | 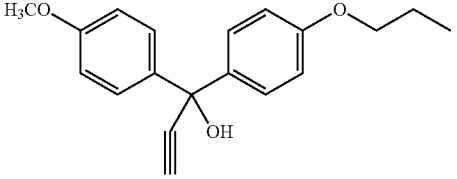 [SMILES: C#CC(O)(c1ccc(OC)cc1)c1ccc(OCCC)cc1] |

TABLE 11-continued
| | | | |
|---|---|---|---|
| 31 | No. 16 | 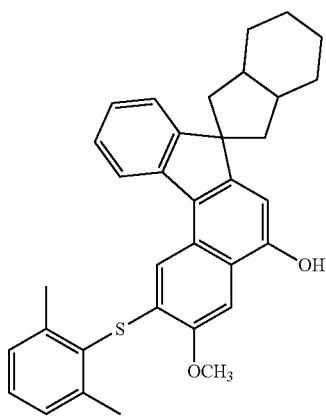 [SMILES: COc1cc2c(O)cc3c(c2cc1Sc1c(C)cccc1C)-c1ccccc1C31CC2CCCCC2C1] | 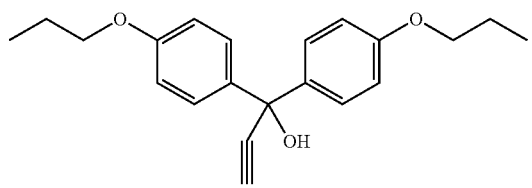 [SMILES: C#CC(O)(c1ccc(OCCC)cc1)c1ccc(OCCC)cc1] |
| Ex. No. | Compound No. | Product (chromene compound) | Yield (%) |
|---|---|---|---|
| 28 | No. 13 | 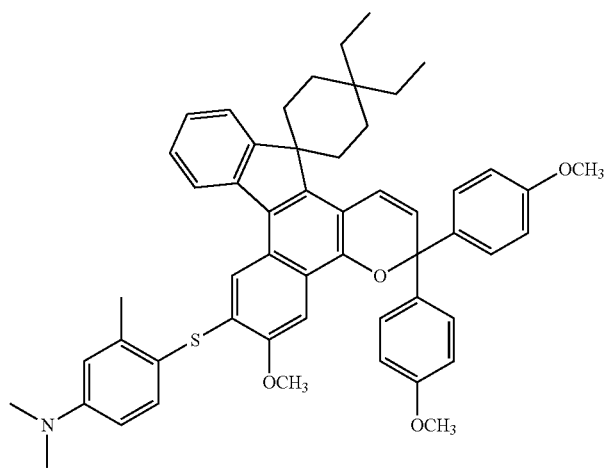 [SMILES: CCC1(CC)CCC2(CC1)c1ccccc1-c1c2c2c(c3cc(OC)c(Sc4ccc(N(C)C)cc4C)cc13)OC(c1ccc(OC)cc1)(c1ccc(OC)cc1)C=C2] | 75 |
| 29 | No. 14 | 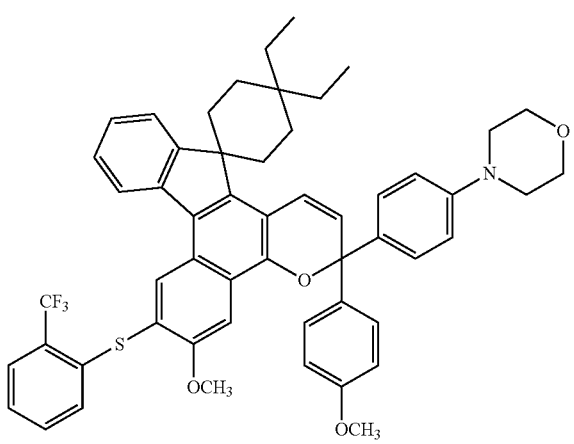 [SMILES: CCC1(CC)CCC2(CC1)c1ccccc1-c1c2c2c(c3cc(OC)c(Sc4ccccc4C(F)(F)F)cc13)OC(c1ccc(OC)cc1)(c1ccc(N3CCOCC3)cc1)C=C2] | 66 |

TABLE 11-continued
| | | | | |
|---|---|---|---|---|
| 30 | No. 15 | 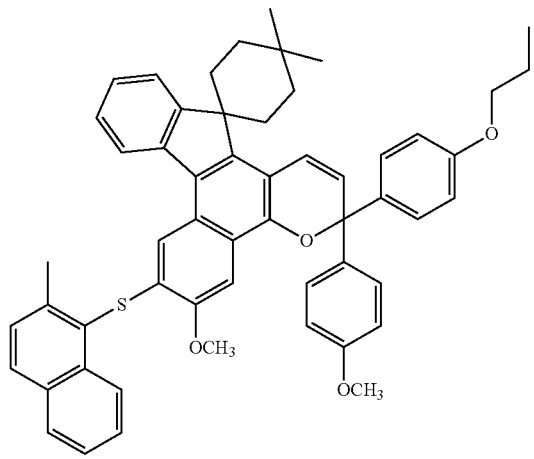 [SMILES: CCCOc1ccc(C2(c3ccc(OC)cc3)C=Cc3c4c(c5cc(Sc6c(C)ccc7ccccc67)c(OC)cc5c3O2)-c2ccccc2C42CCC(C)(C)CC2)cc1] | | 76 |
| 31 | No. 16 | 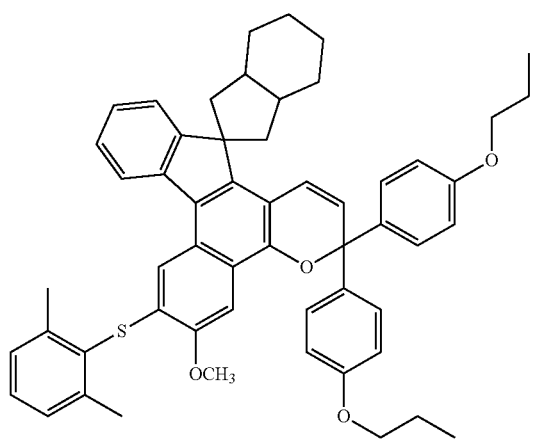 [SMILES: CCCOc1ccc(C2(c3ccc(OCCC)cc3)C=Cc3c4c(c5cc(Sc6c(C)cccc6C)c(OC)cc5c3O2)-c2ccccc2C42CC3CCCCC3C2)cc1] | | 76 |
Ex.: Example
TABLE 12
| | | Raw materials | |
|---|---|---|---|
| Ex. No. | Compound No. | Naphthol compound | Propargyl alcohol compound |
| 32 | No. 17 | 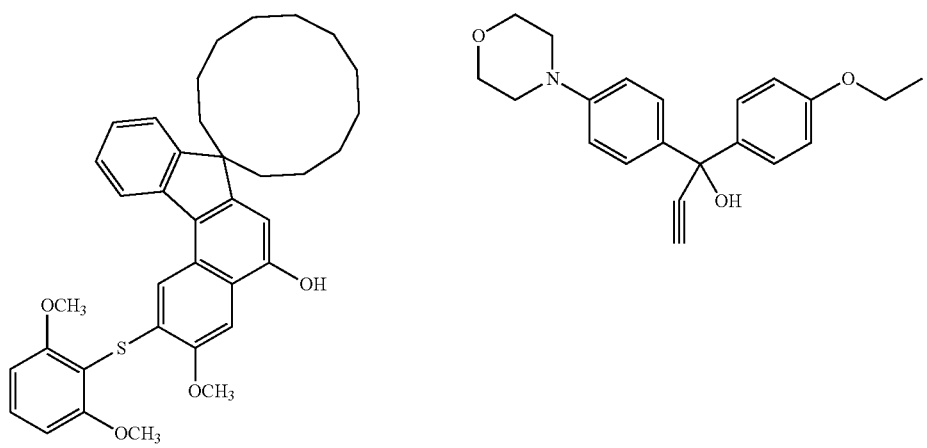 | |

TABLE 12-continued
| | | | |
|---|---|---|---|
| 33 | No. 18 | 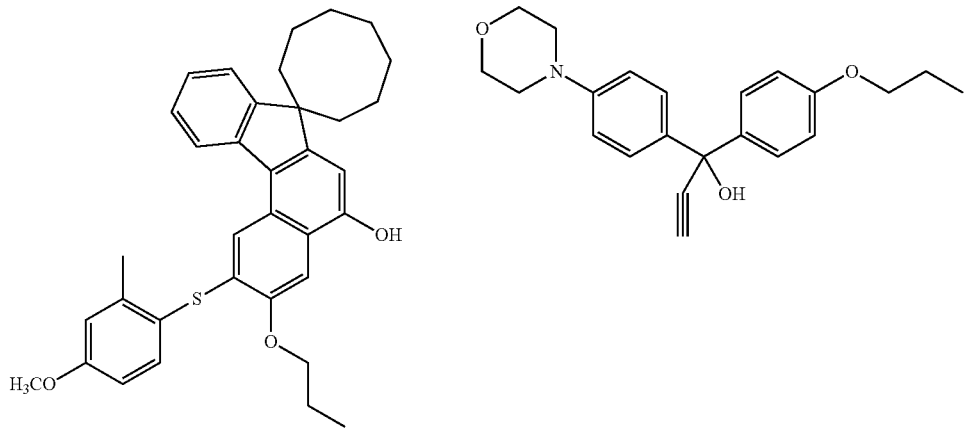 | |
| 34 | No. 19 | 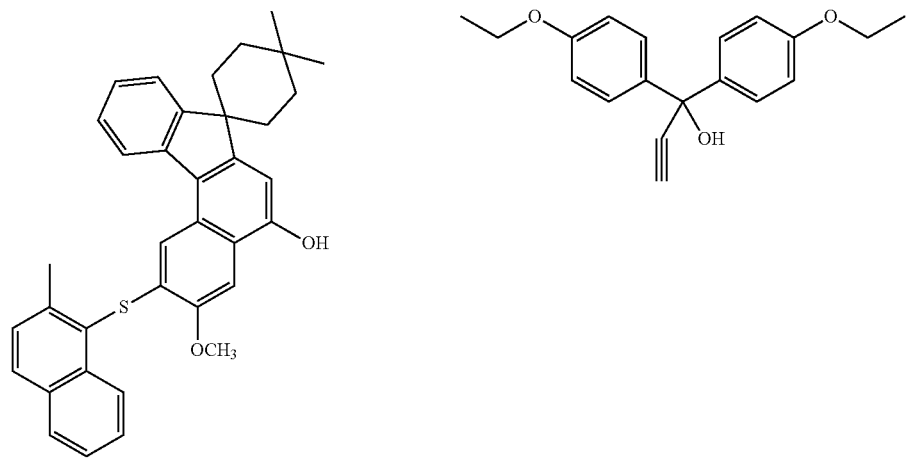 | |
| 35 | No. 20 | 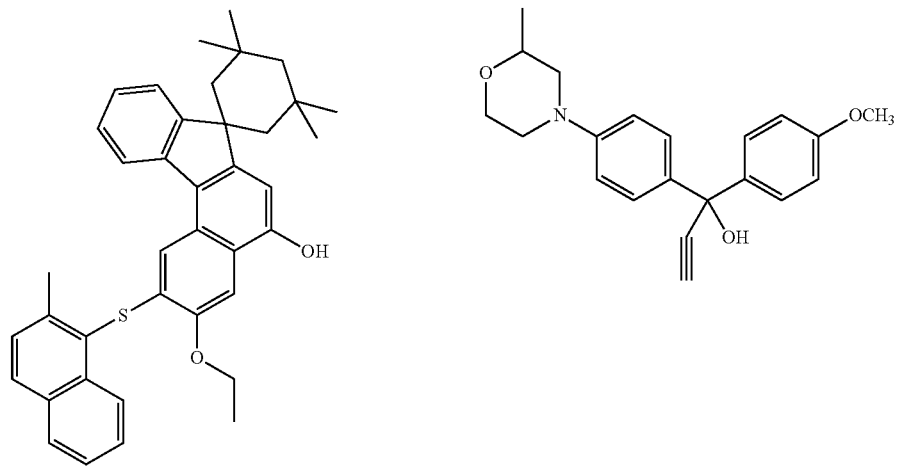 | |

TABLE 12-continued

| Ex. No. | Compound No. | Product (chromene compound) | Yield (%) |
|---|---|---|---|
| 32 | No. 17 | | 74 |
| 33 | No. 18 | | 73 |
| 34 | No. 19 | | 73 |

TABLE 12-continued
| 35 | No. 20 | 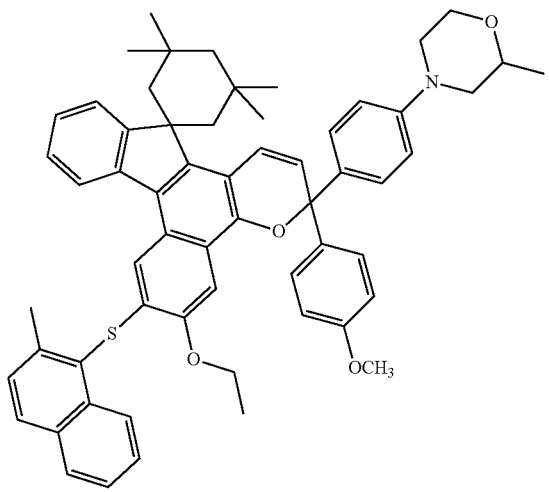 [SMILES: CCOc1cc2c3c(c4c(c2cc1Sc1c(C)ccc2ccccc12)-c1ccccc1C41CC(C)(C)CC(C)(C)C1)C=CC(c1ccc(OC)cc1)(c1ccc(N2CCOC(C)C2)cc1)O3] | 70 |
Ex.: Example
TABLE 13
| | | Raw materials | |
|---|---|---|---|
| Ex. No. | Co. No. | Naphthol compound | Propargyl alcohol compound |
| 36 | No. 21 | | |
| 37 | No. 22 | | |

TABLE 13-continued
| 38 | No. 23 | 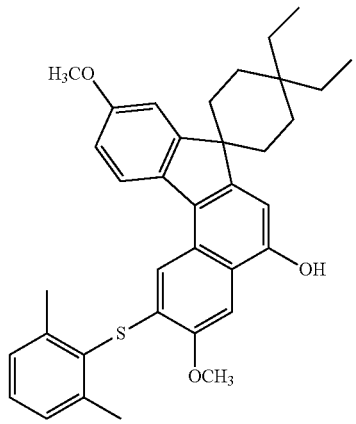 [SMILES: CCC1(CC)CCC2(CC1)c1cc(OC)ccc1-c1c2cc(O)c2cc(OC)c(Sc3c(C)cccc3C)cc12] | 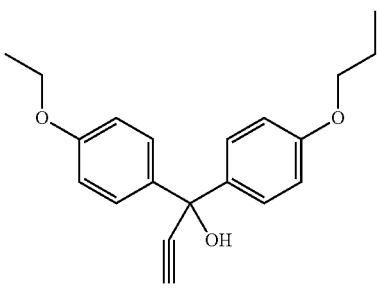 [SMILES: C#CC(O)(c1ccc(OCC)cc1)c1ccc(OCCC)cc1] |
| 39 | No. 24 | 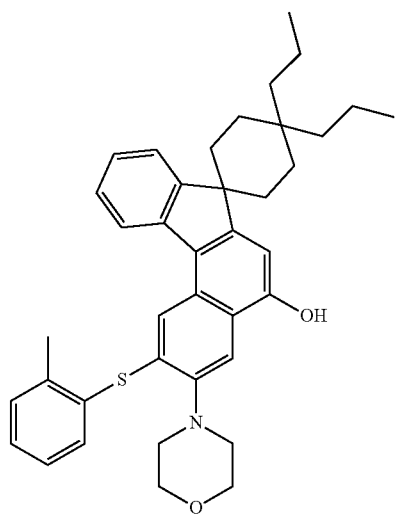 [SMILES: CCCC1(CCC)CCC2(CC1)c1ccccc1-c1c2cc(O)c2cc(N3CCOCC3)c(Sc3ccccc3C)cc12] | 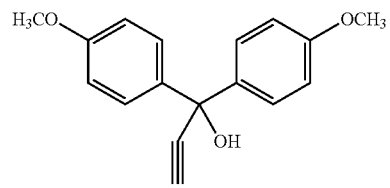 |
| Ex. No. | Co. No. | Product (chromene compund) | Yield (%) |
|---|---|---|---|
| 36 | No. 21 | 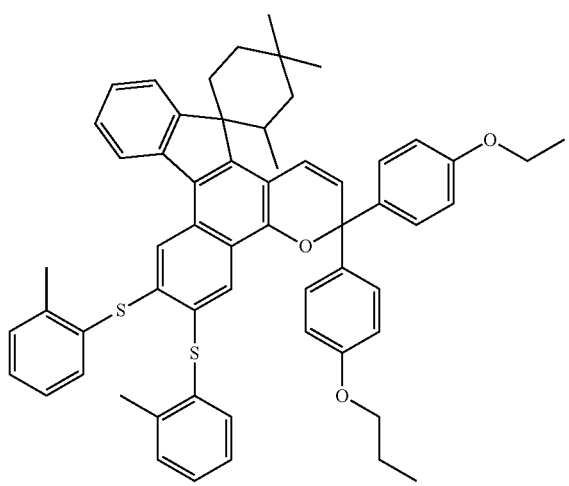 [SMILES: CCCOc1ccc(C2(c3ccc(OCC)cc3)C=Cc3c4c(c5cc(Sc6ccccc6C)c(Sc6ccccc6C)cc5c3O2)-c2ccccc2C42CCC(C)(C)CC2C)cc1] | 71 |

TABLE 13-continued
| 37 | No. 22 | 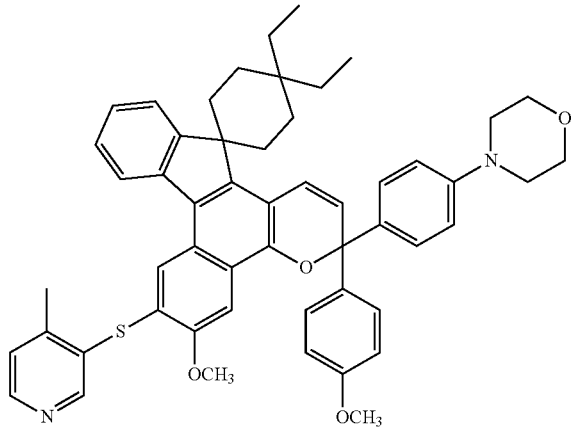 [SMILES: CCC1(CC)CCC2(CC1)c1ccccc1-c1c2c2c(c3cc(OC)c(Sc4cnccc4C)cc13)OC(c1ccc(OC)cc1)(c1ccc(N3CCOCC3)cc1)C=C2] | 68 |
| 38 | No. 23 | 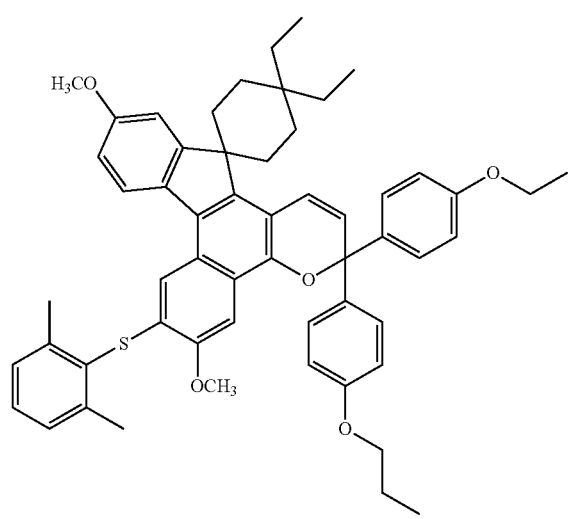 [SMILES: CCCOc1ccc(C2(c3ccc(OCC)cc3)C=Cc3c4c(c5cc(Sc6c(C)cccc6C)c(OC)cc5c3O2)-c2ccc(OC)cc2C42CCC(CC)(CC)CC2)cc1] | 65 |
| 39 | No. 24 | 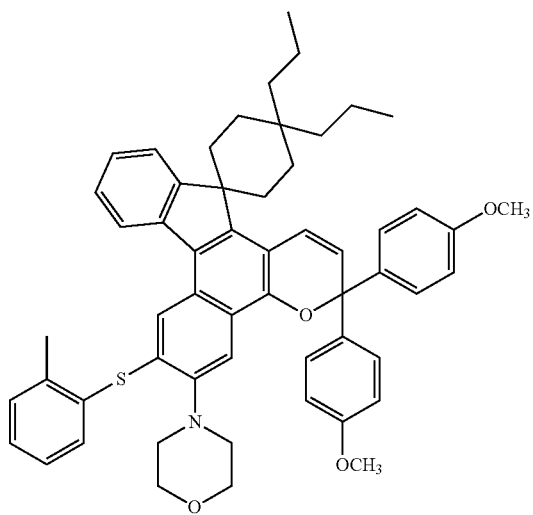 [SMILES: CCCC1(CCC)CCC2(CC1)c1ccccc1-c1c2c2c(c3cc(N4CCOCC4)c(Sc4ccccc4C)cc13)OC(c1ccc(OC)cc1)(c1ccc(OC)cc1)C=C2] | 69 |
Ex.: Example
Co. No.: Compund Number TABLE 14
| Ex. No. | Compound No. | Raw materials | |
| --- | --- | --- | --- |
| | | Naphthol compound | Propargyl alcohol compound |
| 40 | No. 25 | 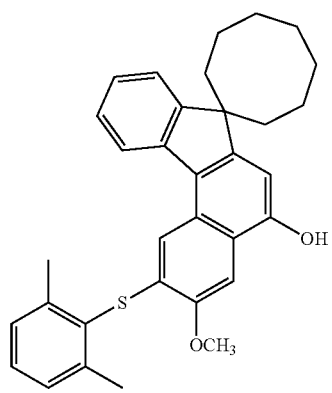 [SMILES: COc1cc2c(O)cc3c(c2cc1Sc1c(C)cccc1C)-c1ccccc1C31CCCCCCC1] | 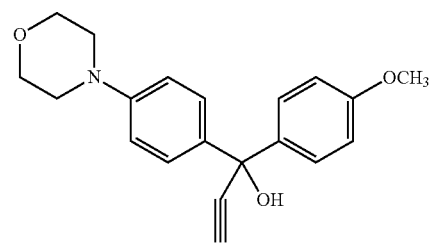 [SMILES: C#CC(O)(c1ccc(OC)cc1)c1ccc(N2CCOCC2)cc1] |
| 41 | No. 26 | 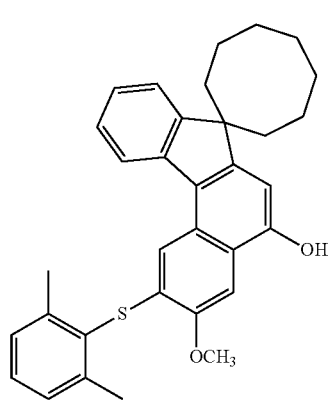 [SMILES: COc1cc2c(O)cc3c(c2cc1Sc1c(C)cccc1C)-c1ccccc1C31CCCCCCC1] | 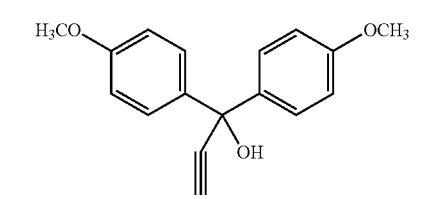 |
| 42 | No. 27 | 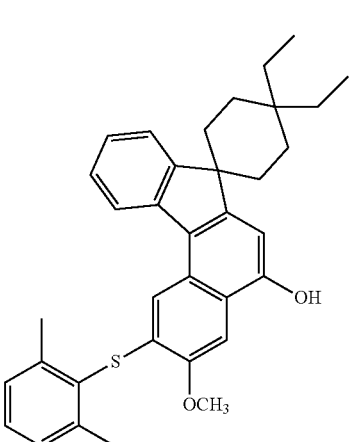 | 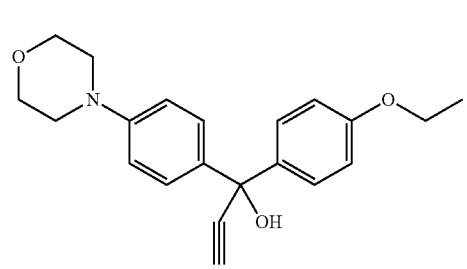 [SMILES: C#CC(O)(c1ccc(OCC)cc1)c1ccc(N2CCOCC2)cc1] |

TABLE 14-continued
| Ex. No. | Compound No. | Product (chromene compound) | Yield (%) |
|---|---|---|---|
| 43 | No. 28 | 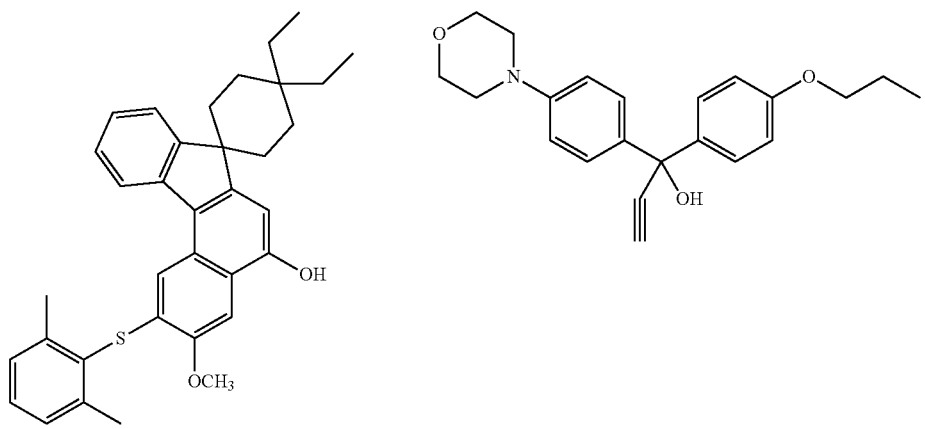 | |
| 40 | No. 25 | 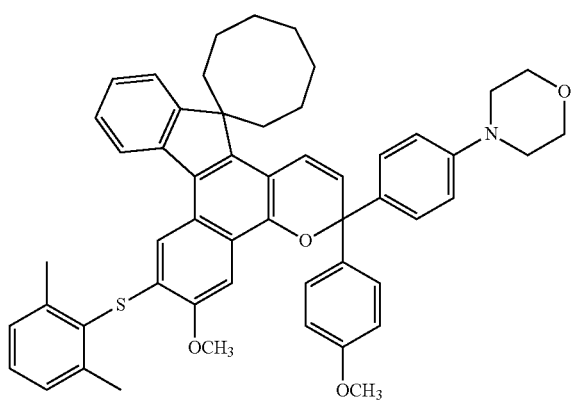 [SMILES: COc1ccc(C2(c3ccc(N4CCOCC4)cc3)C=Cc3c4c(c5cc(Sc6c(C)cccc6C)c(OC)cc5c3O2)-c2ccccc2C42CCCCCCC2)cc1] | 72 |
| 41 | No. 26 | 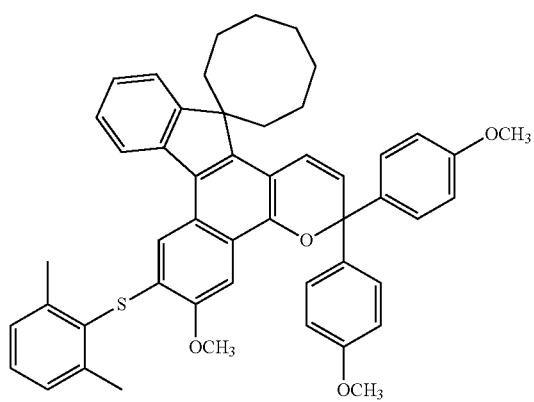 [SMILES: COc1ccc(C2(c3ccc(OC)cc3)C=Cc3c4c(c5cc(Sc6c(C)cccc6C)c(OC)cc5c3O2)-c2ccccc2C42CCCCCCC2)cc1] | 73 |

TABLE 14-continued
| 42 | No. 27 | 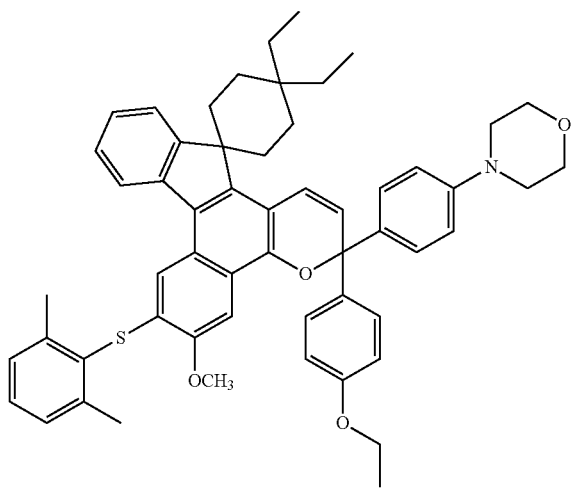 [SMILES: CCOc1ccc(C2(c3ccc(N4CCOCC4)cc3)C=Cc3c4c(c5cc(Sc6c(C)cccc6C)c(OC)cc5c3O2)-c2ccccc2C42CCC(CC)(CC)CC2)cc1] | 76 |
| 43 | No. 28 | 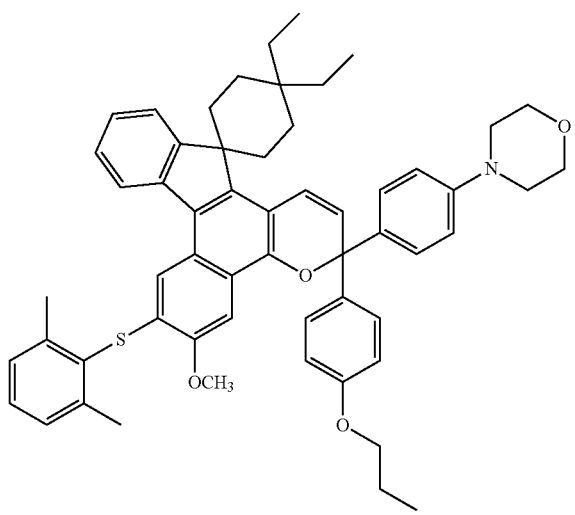 [SMILES: CCCOc1ccc(C2(c3ccc(N4CCOCC4)cc3)C=Cc3c4c(c5cc(Sc6c(C)cccc6C)c(OC)cc5c3O2)-c2ccccc2C42CCC(CC)(CC)CC2)cc1] | 75 |
Ex.: Example
TABLE 15
| | Com- | Raw materials | |
| Ex. No. | pound No. | Naphthol compound | Propargyl alcohol compound |
|---|---|---|---|
| 44 | No. 29 | | |

TABLE 15-continued
| 45 | No. 30 | 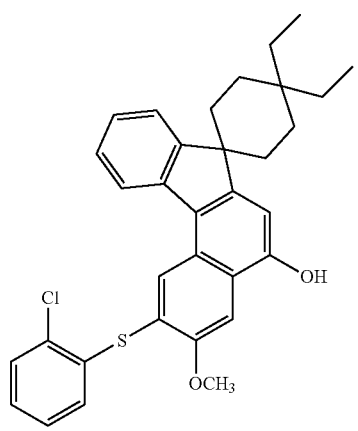 [SMILES: CCC1(CC)CCC2(CC1)c1ccccc1-c1c2cc(O)c2cc(OC)c(Sc3ccccc3Cl)cc12] | 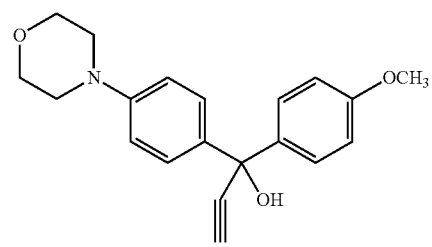 [SMILES: C#CC(O)(c1ccc(OC)cc1)c1ccc(N2CCOCC2)cc1] |
| 46 | No. 31 | 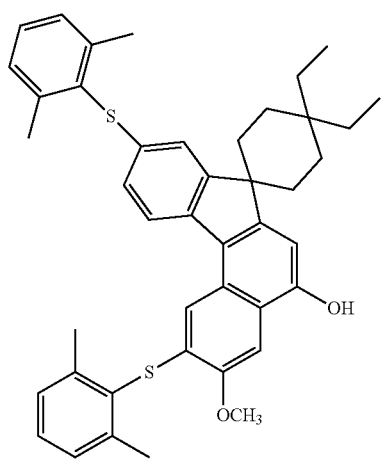 [SMILES: CCC1(CC)CCC2(CC1)c1cc(Sc3c(C)cccc3C)ccc1-c1c2cc(O)c2cc(OC)c(Sc3c(C)cccc3C)cc12] | 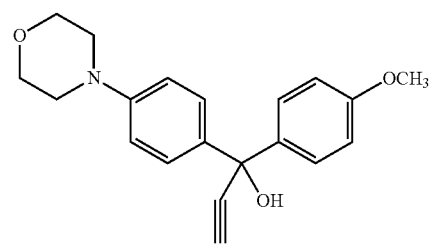 [SMILES: C#CC(O)(c1ccc(OC)cc1)c1ccc(N2CCOCC2)cc1] |
| Ex. No. | Compound No. | Product (chromene compound) | Yield (%) |
|---|---|---|---|
| 44 | No. 29 | 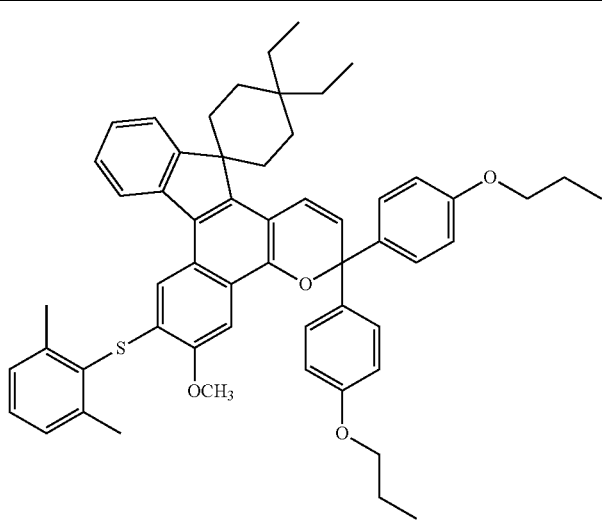 | 73 |

TABLE 15-continued
45  No. 30  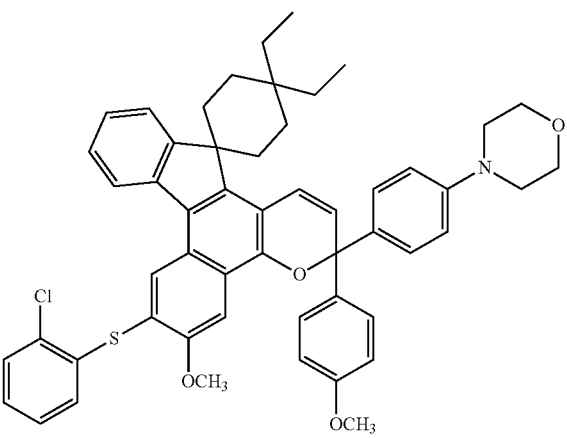 [SMILES: CCC1(CC)CCC2(CC1)c1ccccc1-c1c2c2c(c3cc(OC)c(Sc4ccccc4Cl)cc13)OC(c1ccc(OC)cc1)(c1ccc(N3CCOCC3)cc1)C=C2]  71
46  No. 31  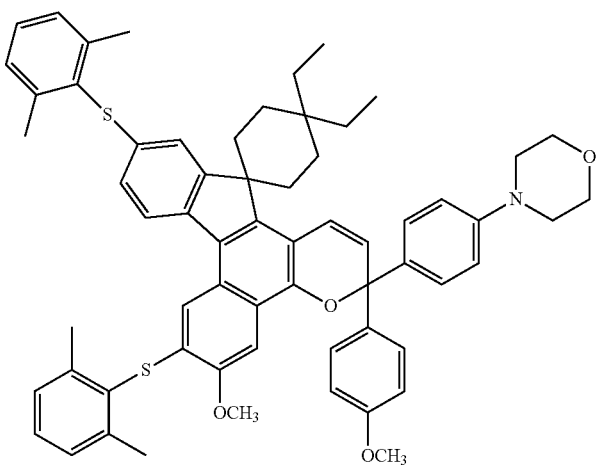 [SMILES: CCC1(CC)CCC2(CC1)c1cc(Sc3c(C)cccc3C)ccc1-c1c2c2c(c3cc(OC)c(Sc4c(C)cccc4C)cc13)OC(c1ccc(OC)cc1)(c1ccc(N3CCOCC3)cc1)C=C2]  68
Ex.: Example
TABLE 16
| | | Calculated values | | | | Experimental values | | | | |
|---|---|---|---|---|---|---|---|---|---|---|
| Ex. No. | Compound No. | C | H | N | S | C | H | N | S | $^1$H-NMR (ppm) |
| 24 | No. 9 | 80.79 | 6.78 | | 4.15 | 80.78 | 6.78 | | 4.10 | δ5.5-9.0 19H |
| | | | | | | | | | | δ0.5-4.5 33H |
| 25 | No. 10 | 79.77 | 6.94 | 1.69 | 3.87 | 79.78 | 7.00 | 1.68 | 3.77 | δ5.5-9.0 19H |
| | | | | | | | | | | δ0.5-4.5 42H |
| 26 | No. 11 | 79.96 | 7.18 | 1.64 | 3.75 | 79.88 | 7.18 | 1.60 | 3.80 | δ5.5-9.0 19H |
| | | | | | | | | | | δ0.5-4.5 42H |
| 27 | No. 12 | 79.76 | 7.18 | 1.64 | 3.75 | 79.72 | 7.15 | 1.66 | 3.77 | δ5.5-9.0 19H |
| | | | | | | | | | | δ0.5-4.5 42H |
| 28 | No. 13 | 79.37 | 6.91 | 1.75 | 4.00 | 79.45 | 7.00 | 1.73 | 3.98 | δ5.5-9.0 18H |
| | | | | | | | | | | δ0.5-4.5 37H |
| 29 | No. 14 | 74.72 | 6.04 | 1.61 | 3.69 | 74.77 | 6.08 | 1.62 | 3.71 | δ5.5-9.0 20H |
| | | | | | | | | | | δ0.5-4.5 32H |
| 30 | No. 15 | 81.65 | 6.48 | | 3.96 | 81.58 | 6.49 | | 3.95 | δ5.5-9.0 22H |
| | | | | | | | | | | δ0.5-4.5 30H |
| 31 | No. 16 | 81.24 | 6.94 | | 3.94 | 81.20 | 6.91 | | 3.90 | δ5.5-9.0 19H |
| | | | | | | | | | | δ0.5-4.5 37H |
| 32 | No. 17 | 77.21 | 7.04 | 1.55 | 3.55 | 77.22 | 7.10 | 1.50 | 3.52 | δ5.5-9.0 19H |
| | | | | | | | | | | δ0.5-4.5 44H |
| 33 | No. 18 | 78.50 | 7.05 | 1.61 | 3.68 | 78.59 | 7.07 | 1.59 | 3.62 | δ5.5-9.0 19H |
| | | | | | | | | | | δ0.5-4.5 42H |
| 34 | No. 19 | 81.65 | 6.48 | | 3.96 | 81.63 | 6.39 | | 4.01 | δ5.5-9.0 22H |
| | | | | | | | | | | δ0.5-4.5 30H |
| 35 | No. 20 | 80.77 | 6.89 | 1.57 | 3.59 | 80.71 | 6.79 | 1.51 | 3.57 | δ5.5-9.0 22H |
| | | | | | | | | | | δ0.5-4.5 39H |
| 36 | No. 21 | 80.55 | 6.61 | | 7.31 | 80.60 | 6.65 | | 7.29 | δ5.5-9.0 24H |
| | | | | | | | | | | δ0.5-4.5 34H |

TABLE 16-continued

|  |  | Calculated values | | | | Experimental values | | | | |
|---|---|---|---|---|---|---|---|---|---|---|
| Ex. No. | Compound No. | C | H | N | S | C | H | N | S | $^1$H-NMR (ppm) |
| 37 | No. 22 | 78.10 | 6.68 | 3.44 | 7.85 | 78.05 | 6.62 | 3.44 | 7.82 | δ5.5-9.0 19H |
|  |  |  |  |  |  |  |  |  |  | δ0.5-4.5 35H |
| 38 | No. 23 | 79.58 | 7.16 |  | 3.79 | 79.55 | 7.12 |  | 3.75 | δ5.5-9.0 18H |
|  |  |  |  |  |  |  |  |  |  | δ0.5-4.5 42H |
| 39 | No. 24 | 79.85 | 7.12 | 1.73 | 3.85 | 79.87 | 7.06 | 1.66 | 3.81 | δ5.5-9.0 20H |
|  |  |  |  |  |  |  |  |  |  | δ0.5-4.5 39H |
| 40 | No. 25 | 79.57 | 6.68 | 1.75 | 4.01 | 79.57 | 6.66 | 1.76 | 4.04 | δ5.5-9.0 19H |
|  |  |  |  |  |  |  |  |  |  | δ0.5-4.5 34H |
| 41 | No. 26 | 80.61 | 6.49 |  | 4.30 | 80.58 | 6.52 |  | 4.32 | δ5.5-9.0 19H |
|  |  |  |  |  |  |  |  |  |  | δ0.5-4.5 29H |
| 42 | No. 27 | 79.87 | 7.06 | 1.66 | 3.81 | 79.39 | 6.72 | 1.51 | 3.57 | δ5.5-9.0 19H |
|  |  |  |  |  |  |  |  |  |  | δ0.5-4.5 40H |
| 43 | No. 28 | 79.96 | 7.18 | 1.64 | 3.75 | 79.9 | 7.21 | 1.68 | 3.72 | δ5.5-9.0 19H |
|  |  |  |  |  |  |  |  |  |  | δ0.5-4.5 42H |
| 44 | No. 29 | 81.12 | 7.29 |  | 3.87 | 81.15 | 7.32 |  | 3.82 | δ5.5-9.0 19H |
|  |  |  |  |  |  |  |  |  |  | δ0.5-4.5 41H |
| 45 | No. 30 | 76.28 | 6.28 | 1.68 | 3.84 | 76.32 | 6.32 | 1.71 | 3.80 | δ5.5-9.0 20H |
|  |  |  |  |  |  |  |  |  |  | δ0.5-4.5 32H |
| 46 | No. 31 | 78.47 | 6.79 | 1.45 | 6.65 | 78.45 | 6.70 | 1.42 | 6.61 | δ5.5-9.0 22H |
|  |  |  |  |  |  |  |  |  |  | δ0.5-4.5 43H |

Ex.: Example

Examples 47 to 69

Evaluation of Physical Properties of Photochromic Plastic Lens Manufactured by Coating Method Photochromic lenses were manufactured and their characteristic properties were evaluated in the same manner as in Example 1. The results are shown in Tables 17 and 18.

TABLE 17

|  | Compound No. | Maximum absorption wavelength λmax (nm) | Color optical density $A_0$ | Double peak characteristic $A_Y/A_B$ | Fading half period τ½ (sec) | Absorption end $λ_0$ (nm) | Residual rate $(A_{50}/A_0) \times 100$ (%) | Heat resistance | |
|---|---|---|---|---|---|---|---|---|---|
|  |  |  |  |  |  |  |  | ΔYI | $1-(A'_Y/A'_B)/(A_Y/A_B)$ |
| Ex. 47 | No. 9 | 462 | 1.03 | 1.29 | 81 | 410 | 89 | 1 | 0 |
|  |  | 569 | 0.8 |  | 82 |  | 89 |  |  |
| Ex. 48 | No. 10 | 480 | 0.81 | 1.03 | 78 | 409 | 89 | 1.1 | 0 |
|  |  | 589 | 0.79 |  | 79 |  | 89 |  |  |
| Ex. 49 | No. 11 | 460 | 0.77 | 0.97 | 78 | 401 | 88 | 0.5 | 0 |
|  |  | 567 | 0.79 |  | 78 |  | 89 |  |  |
| Ex. 50 | No. 12 | 480 | 0.76 | 0.97 | 79 | 409 | 88 | 0.9 | 0 |
|  |  | 589 | 0.78 |  | 78 |  | 89 |  |  |
| Ex. 51 | No. 13 | 482 | 0.77 | 1.00 | 82 | 412 | 85 | 1.3 | 0.07 |
|  |  | 591 | 0.77 |  | 82 |  | 84 |  |  |
| Ex. 52 | No. 14 | 476 | 0.7 | 0.92 | 77 | 409 | 90 | 1.8 | 0.1 |
|  |  | 583 | 0.76 |  | 77 |  | 90 |  |  |
| Ex. 53 | No. 15 | 466 | 1.01 | 1.28 | 88 | 412 | 87 | 1.1 | 0.08 |
|  |  | 576 | 0.79 |  | 89 |  | 87 |  |  |
| Ex. 54 | No. 16 | 462 | 1.03 | 1.34 | 95 | 411 | 85 | 1 | 0 |
|  |  | 571 | 0.77 |  | 95 |  | 84 |  |  |
| Ex. 55 | No. 17 | 475 | 0.84 | 0.99 | 210 | 412 | 84 | 1.1 | 0 |
|  |  | 583 | 0.85 |  | 210 |  | 84 |  |  |
| Ex. 56 | No. 18 | 475 | 0.77 | 1.00 | 85 | 410 | 88 | 1.1 | 0.08 |
|  |  | 585 | 0.77 |  | 85 |  | 88 |  |  |
| Ex. 57 | No. 19 | 462 | 1.05 | 1.35 | 90 | 409 | 86 | 1.2 | 0.08 |
|  |  | 571 | 0.78 |  | 90 |  | 86 |  |  |
| Ex. 58 | No. 20 | 476 | 0.58 | 0.98 | 43 | 410 | 87 | 1.2 | 0.09 |
|  |  | 586 | 0.59 |  | 42 |  | 87 |  |  |

Ex.: Example

TABLE 18

| | Compound No. | Maximum absorption wavelength λmax (nm) | Color optical density $A_0$ | Double peak characteristic $A_Y/A_B$ | Fading half period $\tau_{1/2}$ (sec) | Absorption end $\lambda_0$ (nm) | Residual rate $(A_{50}/A_0) \times 100(\%)$ | Heat resistance ΔYI | $1-(A'_Y/A'_B)/(A_Y/A_B)$ |
|---|---|---|---|---|---|---|---|---|---|
| Ex. 59 | No. 21 | 462 | 0.89 | 1.44 | 92 | 410 | 86 | 1.1 | 0.1 |
| | | 571 | 0.62 | | 91 | | 86 | | |
| Ex. 60 | No. 22 | 461 | 0.89 | 1.44 | 93 | 411 | 78 | 1.2 | 0.09 |
| | | 570 | 0.62 | | 93 | | 78 | | |
| Ex. 61 | No. 23 | 460 | 0.98 | 1.51 | 99 | 410 | 80 | 1.1 | 0.01 |
| | | 571 | 0.65 | | 100 | | 80 | | |
| Ex. 62 | No. 24 | 470 | 0.67 | 1.40 | 35 | 402 | 87 | 0.6 | 0.01 |
| | | 568 | 0.48 | | 35 | | 87 | | |
| Ex. 63 | No. 25 | 475 | 0.78 | 1.01 | 86 | 410 | 88 | 1 | 0 |
| | | 585 | 0.77 | | 85 | | 88 | | |
| Ex. 64 | No. 26 | 460 | 0.88 | 1.42 | 92 | 409 | 89 | 0.9 | 0 |
| | | 570 | 0.62 | | 92 | | 88 | | |
| Ex. 65 | No. 27 | 480 | 0.76 | 0.97 | 80 | 409 | 88 | 1 | 0 |
| | | 589 | 0.78 | | 80 | | 88 | | |
| Ex. 66 | No. 28 | 479 | 0.76 | 0.97 | 83 | 410 | 88 | 1 | 0 |
| | | 587 | 0.78 | | 83 | | 87 | | |
| Ex. 67 | No. 29 | 462 | 1.03 | 1.30 | 89 | 410 | 86 | 1 | 0 |
| | | 569 | 0.79 | | 89 | | 86 | | |
| Ex. 68 | No. 30 | 480 | 0.79 | 1.01 | 78 | 409 | 85 | 1.8 | 0.8 |
| | | 588 | 0.78 | | 79 | | 84 | | |
| Ex. 69 | No. 31 | 481 | 0.81 | 1.03 | 82 | 413 | 81 | 1.7 | 0.7 |
| | | 588 | 0.79 | | 81 | | 80 | | |

Ex.: Example

It is understood that the photochromic plastic lenses of Example 47 to 69 which were manufactured by using the chromene compounds of the present invention are superior in fading speed and durability to the photochromic plastic lenses of Comparative Example 1 (chromene compound represented by the above formula (A)), Comparative Example 2 (chromene compound represented by the above formula (B)), Comparative Example 3 (chromene compound represented by the above formula (C)) and Comparative Example 4 (chromene compound represented by the above formula (D)) while having high heat resistance.

Examples 70, 75 and 83

Production of Naphthol Compounds

Example 70 is a production example of the naphthol compound of Example 24 in Table 10, Example 75 is a production example of the naphthol compound of Example 31 in Table 11, and Example 83 is a production example of the naphthol compound of Example 40 in Table 14, and these naphthol compounds were synthesized by the same process as in Example 17. When the structures of the obtained products were analyzed by using the same structure confirming means as in Example 17, it was confirmed that they were naphthol compounds used in Examples shown in tables. Table 19 shows the elemental analysis values, calculated values obtained from the structural formulas and characteristic $^1$H-NMR spectra of these compounds.

Example 71

Production of Naphthol Compound

Example 71 is a production example of the naphthol compound of Example 26 in Table 10, and the naphthol compound was synthesized by the same process as in Example 18. When the structure of the obtained product was analyzed by using the same structure confirming means as in Example 17, it was confirmed that it was a naphthol compound used in Example shown in the table. Table 19 shows the elemental analysis values, calculated values obtained from the structural formula and characteristic $^1$H-NMR spectrum of this compound.

Example 72

Production of Naphthol Compound

Example 72 is a production example of the naphthol compound of Example 28 in Table 11.

85.64 g (400 mmol) of 4-bromo-N,N,3-trimethylaniline was dissolved in 500 ml of diethyl ether and cooled to −78° C. 275.4 ml (440.0 mmol) of n-butyl lithium (1.6M hexane solution) was added dropwise to this solution and stirred for 30 minutes. 64.1 g of a diethyl ether solution containing 12.82 g (400 mmol) of sulfur was added dropwise to this solution and stirred at 0° C. for 3 hours. After a reaction, diethyl ether was added, the resulting reaction solution was washed with water, the solvent was removed, and the obtained product was purified by column chromatography to obtain a thiobenzene derivative represented by the following formula (38) as 33.7 g (140 mmol, yield of 35%) of a yellow solid.

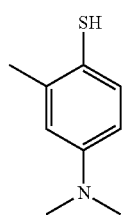

(38)

The obtained thiobenzene derivative and the benzophenone derivative (21) were coupled to each other, and the operation of Example 17 was repeated to obtain a naphthol compound represented by the following formula (39).

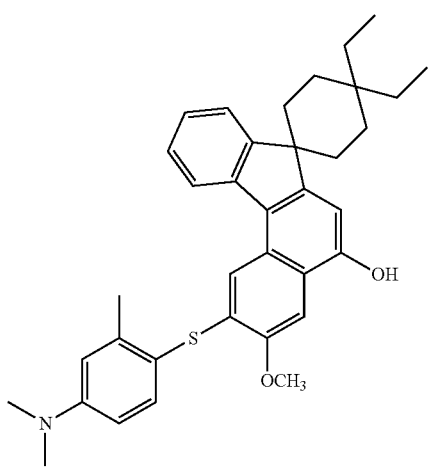

(39)

The structure of this compound was analyzed by using the same structure confirming means as in Example 17 to be confirmed. Table 19 shows the elemental analysis values, calculated values obtained from the structural formula and characteristic $^1$H-NMR spectrum of this compound.

Examples 73, 74, 76, 80, 83 and 84

Production of Naphthol Compounds

Example 73 is a production example of the naphthol compound of Example 29 in Table 11, Example 74 is a production example of the naphthol compound of Example 30 in Table 11, Example 76 is a production example of the naphthol compound of Example 32 in Table 12, Example 80 is a production example of the naphthol compound of Example 37 in Table 13, Example 83 is a production example of the naphthol compound of Example 40 in Table 14, and Example 84 is a production example of the naphthol compound of Example 45 in Table 15. These naphthol compounds were synthesized in the same manner as in Example 72 except that 2-trifluorobromobenzene, 2-methylbromonaphthalene, 1,2-dimethoxythiobenzene, 3-bromo-4-methylpyridine, 2,6-dimethylthiobenzene and 2-chlorobromobenzene were used as a starting material in Example 73, Examples 74, Example 76, Example 80, Example 83 and Example 84, respectively. When the structures of the obtained products were analyzed by using the same structure confirming means as in Example 17, it was confirmed that they were naphthol compounds used in Examples shown in the tables. Table 19 shows the elemental analysis values, calculated values obtained from the structural formulas and characteristic $^1$H-NMR spectra of these compounds.

Example 77

Production of Naphthol Compound

Example 77 is a production example of the naphthol compound of Example 33 in Table 12.

69.7 g (324.2 mmol) of 1-bromo-2-propoxybenzene was added dropwise to a dichloromethane (350 ml) solution containing 51.8 g (388.6 mmol) of aluminum chloride and 45.6 g (324.3 mmol) of benzoyl chloride which was cooled to 0° C. After addition, the resulting solution was stirred for 2 hours. After a reaction, the reaction solution was washed with water, the solvent was removed, and the obtained product was purified by column chromatography to obtain a benzophenone derivative represented by the following formula (40) as 67.3 g (210.7 mmol, yield of 65%) of a yellow solid.

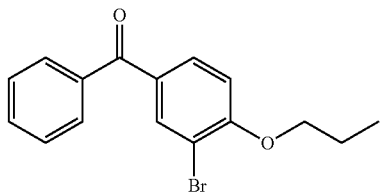

(40)

When the operation of Example 17 was repeated by using the benzophenone derivative represented by the above formula (40) and 4-methoxy-2-methylthiobenzene, a naphthol compound represented by the following formula (41) was obtained.

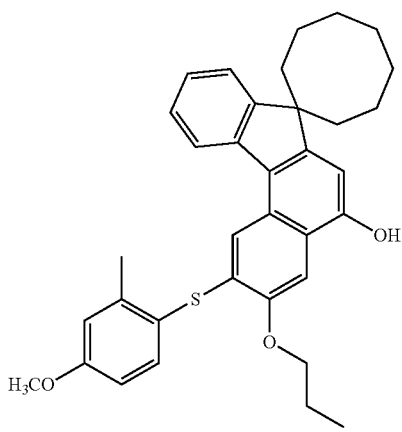

(41)

The structure of the obtained product was analyzed by using the same structure confirming means as in Example 17 to be confirmed. Table 19 shows the elemental analysis values, calculated values obtained from the structural formula and characteristic $^1$H-NMR spectrum of this compound.

Example 82

Production of Naphthol Compound

Example 82 is a production example of the naphthol compound of Example 39 in Table 13, and the naphthol compound was synthesized in the same manner as in Example 17 except that 2-morpholinebromobenzene was used as a starting material. When the structure of the obtained product was analyzed by using the same structure confirming means as in Example 17, it was confirmed that it was a naphthol compound used in Example shown in the table. Table 19 shows the elemental analysis values, calculated values obtained from the structural formula and characteristic $^1$H-NMR spectrum of this compound.

Example 78

Production of Naphthol Compound

Example 78 is a production example of the naphthol compound of Example 35 in Table 12.

8.7 g (357.06 mmol) of Mg and a small amount of iodine were dissolved in 200 ml of THF, and 84.6 g (324.6 mmol) of 1-bromo-4-chloro-3-ethoxybenzene dissolved in 500 ml of THF was added dropwise to the resulting solution. After addition, the resulting mixture was refluxed for 3 hours to prepare a Grignard reagent which was then cooled to room temperature. Thereafter, a Grignard reagent containing 50.2 g (357.06 mmol) of benzoyl chloride was added dropwise to the obtained product and stirred for 5 hours. After a reaction, the reaction solution was washed with water, the solvent was removed, and the obtained product was purified by column chromatography to obtain a benzophenone derivative represented by the following formula (42) as 29.6 g (113.6 mmol, yield of 35%) of a white solid.

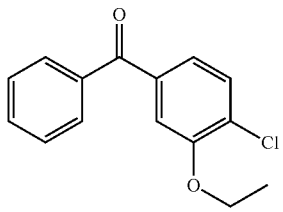

(42)

2-methylthionaphthalene was synthesized from 2-methyl-bromonaphthalene in the same manner as in Example 28, and the operation of Example 18 was repeated by using this to obtain a naphthol compound represented by the following formula (43).

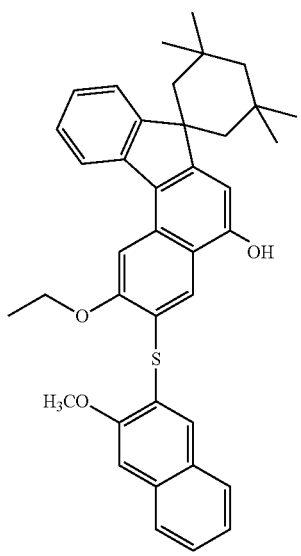

(43)

The structure of this compound was analyzed by using the same structure confirming means as in Example 17 to be confirmed. Table 19 shows the elemental analysis values, calculated values obtained from the structural formula and characteristic $^1$H-NMR spectrum of this compound.

Example 79

Production of Naphthol Compound

Example 79 is a production example of the naphthol compound of Example 36 in Table 13.

94.4 g (400 mmol) of o-dibromobenzene, 221.2 g (1600.0 mmol) of N-ethyl-N,N-diisopropylamine, 7.3 g (8.0 mmol) of tris(dibenzylideneacetone)dipalladium, 8.9 g (16.0 mmol) of 1,-bis(diphenylphosphino) ferrocene and 109.3 g (880 mmol) of 2-dimethylthiobenzene were dissolved in 800 ml of toluene and refluxed for 3 hours in argon atmosphere. After a reaction, the reaction solution was washed with water, the solvent was removed, and the obtained product was purified by column chromatography to obtain a compound represented by the following formula (44) as 122.5 g (380 mmol, yield of 95%) of a yellow solid.

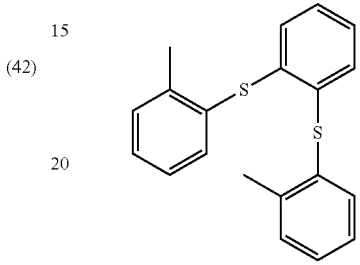

(44)

The obtained product was coupled with benzoyl chloride in the same manner as in Example 17 to obtain a benzophenone derivative represented by the following formula (45) as 29.9 g (70 mmol, yield of 20%) of a yellow solid.

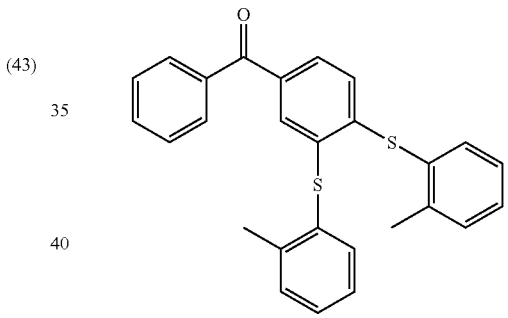

(45)

When the operation of Example 17 was repeated, a naphthol compound represented by the following formula (46) was obtained.

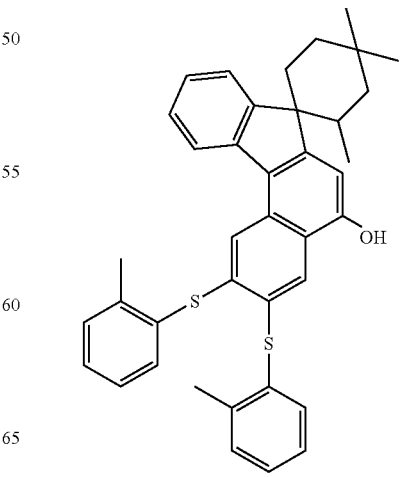

(46)

The structure of the obtained compound was analyzed by using the same structure confirming means as in Example 17 to be confirmed. Table 19 shows the elemental analysis values, calculated values obtained from the structural formula and characteristic $^1$H-NMR spectrum of this compound.

Example 81

Production of Naphthol Compound

Example 81 is a production example of the naphthol compound of Example 38 in Table 13.

60.6 g (324.2 mmol) of 2-bromoanisole was added dropwise to a dichloromethane (350 ml) solution containing 51.8 g (388.6 mmol) of aluminum chloride and 55.31 g (324.3 mmol) of 3-methoxybenzoyl chloride which was cooled to 0° C. After addition, the resulting mixture was stirred for 2 hours. After a reaction, the reaction solution was washed with water, the solvent was removed, and the obtained product was purified by column chromatography to obtain a benzophenone derivative represented by the following formula (47) as 67.7 g (210.7 mmol, yield of 65%) of a yellow solid.

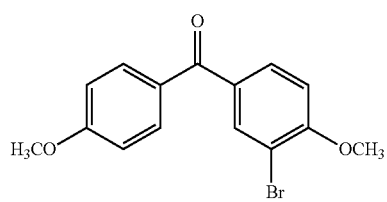

(47)

When the operation of Example 17 was repeated, a naphthol compound represented by the following formula (48) was obtained.

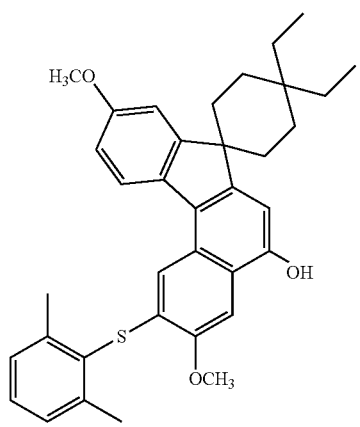

(48)

The structure of the obtained compound was analyzed by using the same structure confirming means as in Example 17 to be confirmed. Table 19 shows the elemental analysis values, calculated values obtained from the structural formula and characteristic $^1$H-NMR spectrum of this compound.

Example 85

Production of Naphthol Compound

Example 85 is a production example of the naphthol compound of Example 46 in Table 15, and this naphthol compound was synthesized in the same manner as in Example 17. The naphthol compound represented by the following formula (49) was obtained from 3-bromobenzoyl chloride as a starting material at a yield of 40%.

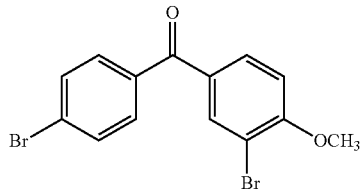

(49)

Thereafter, this naphthol compound was coupled with 1,2-dimethylthiobenzene in the same manner as in Example 17 to obtain a benzophenone derivative represented by the following formula (50) at a yield of 80%.

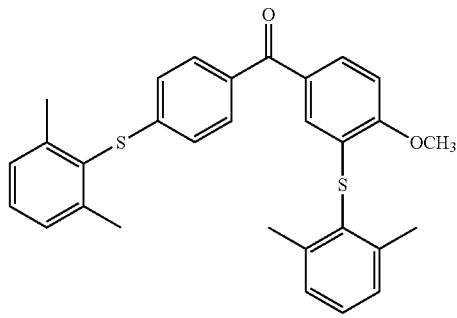

(50)

A naphthol compound represented by the following formula (51) was obtained from the benzophenone derivative of the formula (50) in the same manner as in Example 17.

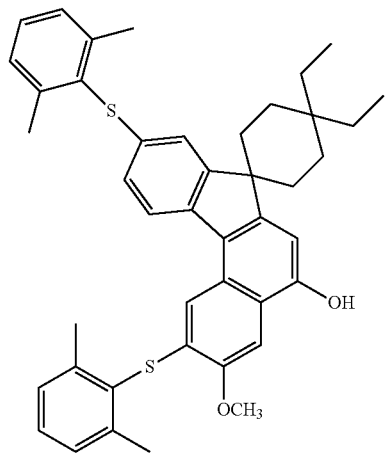

(51)

When the structure of the obtained product was analyzed by using the same structure confirming means as in Example 17, it was confirmed that it was a naphthol compounds used in Example shown in the table. Table 19 shows the elemental analysis values, calculated values obtained from the structural formulas and characteristic $^1$H-NMR spectra of these compounds.

TABLE 19

| Ex. No. | Used chromene compound No.* | Experimental values C | H | N | S | Calculated values C | H | N | S | 1H-NMR (ppm) |
|---|---|---|---|---|---|---|---|---|---|---|
| 70 | 9 | 80.40 | 7.37 | | 6.15 | 80.42 | 7.33 | | 6.13 | δ5.5-9.0 10H<br>δ0.5-4.5 28H |
| 71 | 11 | 80.45 | 7.33 | | 6.14 | 80.42 | 7.33 | | 6.13 | δ5.5-9.0 10H<br>δ0.5-4.5 20H |
| 72 | 13 | 78.36 | 7.49 | 2.54 | 5.81 | 78.45 | 7.55 | 2.48 | 5.72 | δ5.5-9.0 9H<br>δ0.5-4.5 32H |
| 73 | 14 | 72.55 | 5.95 | | 5.65 | 72.57 | 5.91 | | 5.70 | δ5.5-9.0 11H<br>δ0.5-4.5 22H |
| 74 | 15 | 81.47 | 6.47 | | 6.08 | 81.47 | 6.46 | | 6.04 | δ5.5-9.0 13H<br>δ0.5-4.5 21H |
| 75 | 16 | 80.62 | 6.73 | | 6.31 | 80.59 | 6.76 | | 6.33 | δ5.5-9.0 10H<br>δ0.5-4.5 24H |
| 76 | 17 | 76.21 | 7.28 | | 5.49 | 76.25 | 7.26 | | 5.50 | δ5.5-9.0 10H<br>δ0.5-4.5 32H |
| 77 | 18 | 78.04 | 7.15 | | 5.93 | 78.03 | 7.11 | | 5.95 | δ5.5-9.0 10H<br>δ0.5-4.5 28H |
| 78 | 20 | 81.78 | 7.04 | | 5.60 | 81.75 | 7.05 | | 5.50 | δ5.5-9.0 13H<br>δ0.5-4.5 27H |
| 79 | 21 | 79.83 | 6.51 | | 10.93 | 79.82 | 6.53 | | 10.93 | δ5.5-9.0 15H<br>δ0.5-4.5 23H |
| 80 | 22 | 77.76 | 6.92 | 2.75 | 6.29 | 77.70 | 6.93 | 2.78 | 6.27 | δ5.5-9.0 10H<br>δ0.5-4.5 25H |
| 81 | 23 | 78.22 | 7.29 | | 5.80 | 78.24 | 7.31 | | 5.75 | δ5.5-9.0 9H<br>δ0.5-4.5 31H |
| 82 | 24 | 79.10 | 7.70 | 2.37 | 5.41 | 79.15 | 7.66 | 2.37 | 5.42 | δ5.5-9.0 34H<br>δ0.5-4.5 22H |
| 83 | 25 | 78.23 | 6.83 | | 9.97 | 78.22 | 6.85 | | 9.94 | δ5.5-9.0 13H<br>δ0.5-4.5 31H |
| 84 | 30 | 74.91 | 6.29 | 6.05 | 6.06 | 74.95 | 6.24 | 6.1 | 6.06 | δ5.5-9.0 11H<br>δ0.5-4.5 22H |
| 85 | 31 | 78.38 | 7.04 | | 9.73 | 78.32 | 7.01 | | 9.75 | δ5.5-9.0 9H<br>δ0.5-4.5 37H |

*Chromene compound No. obtained by using a naphthol compound
Ex.: Example

Effect of the Invention

The chromene compound of the present invention has high stability at a high temperature, excellent durability and high fading speed as compared with a conventional compound having a sulfur-containing substituent. The chromene compound of the present invention does not yellow and does not change in developed hue upon exposure even when it is dispersed in a polymer solid matrix and kept, for example, at 90° C. for 3 days. Also, even when it is kept at 110° C. for 12 hours, it rarely changes.

Therefore, for instance, when the chromene compound of the present invention is used to manufacture a photochromic lens, a photochromic lens whose thermal damage at the time of a surface treatment is greatly reduced and which exhibits durability high enough to stand long-term use and extremely high performance that it colors deeply swiftly when it moves outside and fades to return to its original color swiftly when it moves back inside from outside can be manufactured.

The invention claimed is:

1. A chromene compound having a basic skeleton represented by the following formula (1):

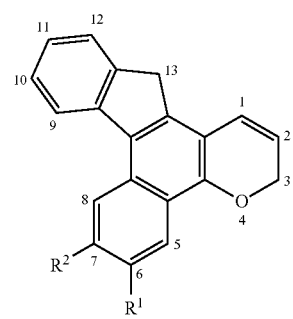

(1)

wherein
(i) Each of $R^1$ and $R^2$ is a sulfur-containing substituent represented by the following formula (2);

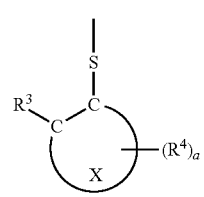

(2)

in the above formula, ring X represented by the following formula is an aromatic hydrocarbon ring or aromatic heterocyclic ring, $R^3$ and $R^4$ are each independently an alkyl group, haloalkyl group, cycloalkyl group, alkoxy group, amino group, heterocyclic group containing a ring member nitrogen atom and bonded to the ring X bonded thereto via the nitrogen atom, halogen atom, aryloxy group or aryl group, "a" is an integer of 0 to 4, and when "a" is 2 to 4, a plurality of $R^4$'s may be the same or different;

(ii) $R^1$ is a sulfur-containing substituent represented by the above formula (2) and $R^2$ is a hydrogen atom, hydroxyl group, alkyl group, haloalkyl group, cycloalkyl group, alkoxy group, amino group, heterocyclic group containing a ring member nitrogen atom and bonded to the 7-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group; or (iii) $R^2$ is a sulfur-containing substituent represented by the above formula (2) and $R^1$ is a hydrogen atom, hydroxyl group, alkyl group, haloalkyl group, cycloalkyl group, alkoxy group, amino group, heterocyclic group containing a ring member nitrogen atom and bonded to the 6-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group.

2. The chromene compound according to claim 1 which is represented by the following formula (3):

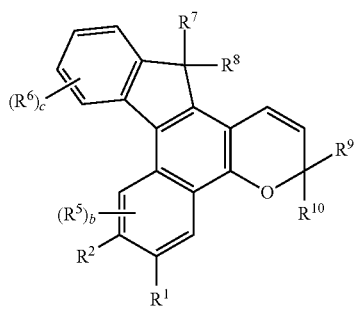

(3)

wherein $R^1$ and $R^2$ are as defined in the above formula (1), $R^5$ and $R^6$ are each independently a hydroxyl group, alkyl group, haloalkyl group, cycloalkyl group, alkoxy group, amino group, heterocyclic group having a ring member nitrogen atom and bonded to an aromatic ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group or sulfur-containing substituent represented by the above formula (2), $R^7$ and $R^8$ are each independently a hydrogen atom, hydroxyl group, alkyl group, haloalkyl group, cycloalkyl group, alkoxy group, alkoxyalkyl group, formyl group, hydroxycarbonyl group, alkylcarbonyl group, alkoxycarbonyl group, halogen atom, aralkyl group, aralkoxy group, aryloxy group or aryl group, and $R^7$ and $R^8$, together with the 13-position carbon atom bonded thereto, may form an aliphatic hydrocarbon ring having 3 to 20 ring member carbon atoms, condensed polycyclic ring having an aromatic hydrocarbon ring or aromatic heterocyclic ring condensed to the aliphatic hydrocarbon ring, heterocyclic ring having 3 to 20 ring member atoms, or condensed polycyclic ring having an aromatic hydrocarbon ring or aromatic heterocylcic ring condensed to the heterocyclic ring, $R^9$ and $R^{10}$ are each independently a group represented by the following formula (4), group represented by the following formula (5), aryl group, heteroaryl group or alkyl group,

(4)

in the above formula, $R^{11}$ is an aryl group or heteroaryl group, $R^{12}$ is a hydrogen atom, alkyl group or halogen atom, and "m" is an integer of 1 to 3;

(5)

in the above formula, $R^{13}$ is an aryl group or heteroaryl group, and "n" is an integer of 1 to 3; $R^9$ and $R^{10}$ may form an aliphatic hydrocarbon ring together with the carbon atom bonded thereto, "b" is an integer of 0 to 2, "c" is an integer of 0 to 4, when "b" is 2, two $R^5$'s may be the same or different, and when "c" is 2 to 4, a plurality of $R^6$'s may be the same or different.

3. A photochromic curable composition comprising the chromene compound of claim 2 and a polymerizable monomer.

4. A photochromic optical article having a polymer molded product comprising the chromene compound of claim 2 dispersed therein as a constituent member.

5. An optical article having an optical substrate all or part of at least one surface of which is covered with a polymer film comprising the chromene compound of claim 2 dispersed therein as a constituent member.

6. The chromene compound according to claim 2, wherein, in the above formula (3), $R^7$ and $R^8$ form an aliphatic hydrocarbon ring together with the 13-position carbon atom bonded thereto, and the aliphatic hydrocarbon ring has 3 to 20 ring member carbon atoms and may have at least one substituent selected from the group consisting of alkyl group, haloalkyl group, cycloalkyl group, alkoxy group, amino group, aralkyl group, aryl group and halogen atom.

7. A photochromic curable composition comprising the chromene compound of claim 6 and a polymerizable monomer.

8. A photochromic optical article having a polymer molded product comprising the chromene compound of claim 6 dispersed therein as a constituent member.

9. An optical article having an optical substrate all or part of at least one surface of which is covered with a polymer film comprising the chromene compound of claim 6 dispersed therein as a constituent member.

10. A photochromic curable composition comprising the chromene compound of claim 1 and a polymerizable monomer.

11. A photochromic optical article having a polymer molded product comprising the chromene compound of claim 1 dispersed therein as a constituent member.

12. The photochromic optical article according to claim 11 which has a yellowness index change (ΔYI) after it is kept at 110° C. for 12 hours of 2 or less and does not substantially change in developed hue at the time of exposure.

13. An optical article having an optical substrate all or part of at least one surface of which is covered with a polymer film comprising the chromene compound of claim 1 dispersed therein as a constituent member.

14. A naphthol compound represented by the following formula (6):

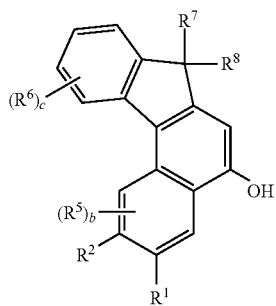

(6)

wherein each of $R^1$ and $R^2$ is a sulfur-containing substituent represented by the following formula (2);

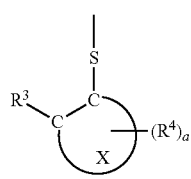

(2)

in the above formula, ring X represented by the following formula is an aromatic hydrocarbon ring or aromatic heterocyclic ring, $R^3$ and $R^4$ are each independently an alkyl group, haloalkyl group, cycloalkyl group, alkoxy group, amino group, heterocyclic group containing a ring member nitrogen atom and bonded to the ring X bonded thereto via the nitrogen atom, halogen atom, aryloxy group or aryl group, "a" is an integer of 0 to 4, and when "a" is 2 to 4, a plurality of $R^4$'s may be the same or different;

(ii) $R^1$ is a sulfur-containing substituent represented by the above formula (2) and $R^2$ is a hydrogen atom, hydroxyl group, alkyl group, haloalkyl group, cycloalkyl group, alkoxy group, amino group, heterocyclic group containing a ring member nitrogen atom and bonded to the 7-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group; or (iii) $R^2$ is a sulfur-containing substituent represented by the above formula (2) and $R^1$ is a hydrogen atom, hydroxyl group, alkyl group, haloalkyl group, cycloalkyl group, alkoxy group, amino group, heterocyclic group containing a ring member nitrogen atom and bonded to the 6-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group;

$R^5$ and $R^6$ are each independently a hydroxyl group, alkyl group, haloalkyl group, cycloalkyl group, alkoxy group, amino group, heterocyclic group having a ring member nitrogen atom and bonded to an aromatic ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group or sulfur-containing substituent represented by the above formula (2), $R^7$ and $R^8$ are each independently a hydrogen atom, hydroxyl group, alkyl group, haloalkyl group, cycloalkyl group, alkoxy group, alkoxyalkyl group, formyl group, hydroxycarbonyl group, alkylcarbonyl group, alkoxycarbonyl group, halogen atom, aralkyl group, aralkoxy group, aryloxy group or aryl group, and $R^7$ and $R^8$, together with the carbon atom bonded thereto, may form an aliphatic hydrocarbon ring having 3 to 20 ring member carbon atoms, condensed polycyclic ring having an aromatic hydrocarbon ring or aromatic heterocyclic ring condensed to the aliphatic hydrocarbon ring, heterocyclic ring having 3 to 20 ring member atoms, or condensed polycyclic ring having an aromatic hydrocarbon ring or aromatic heterocylcic ring condensed to the heterocyclic ring, "b" is an integer of 0 to 2, "c" is an integer of 0 to 4, when "b" is 2, two $R^5$'s may be the same or different, and when "c" is 2 to 4, a plurality of $R^6$'s may be the same or different.

* * * * *